United States Patent [19]

Vogelbacher et al.

[11] Patent Number: 5,246,914
[45] Date of Patent: Sep. 21, 1993

[54] SALICYLOYL (THIO)ETHER DERIVATIVES, THEIR PREPARATION AND INTERMEDIATES FOR THEIR PREPARATION

[75] Inventors: Uwe J. Vogelbacher; Joachim Rheinheimer, both of Ludwigshafen; Thomas Saupe, Sandhausen; Norbert Meyer, Ladenburg; Matthias Gerber, Mutterstadt; Karl-Otto Westphalen, Speyer; Helmut Walter, Obrigheim, all of Fed. Rep. of Germany

[73] Assignee: BASF Aktiengesellschaft, Ludwigshafen, Fed. Rep. of Germany

[21] Appl. No.: 925,649

[22] Filed: Aug. 7, 1992

[30] Foreign Application Priority Data

Aug. 10, 1991 [FRG] Fed. Rep. Germany .. P4126937.3

[51] Int. Cl.$^5$ .................... A01N 43/48; C07D 239/02
[52] U.S. Cl. .................................. 504/242; 504/197; 504/215; 504/216; 504/227; 504/230; 504/243; 544/243; 544/300; 544/301; 544/302; 544/303; 544/304; 544/306
[58] Field of Search ............... 544/243, 300, 310, 318, 544/301–304, 306, 309, 312, 314–316; 71/86, 92; 504/215, 216, 242, 243, 197

[56] References Cited

U.S. PATENT DOCUMENTS

| | | |
|---|---|---|
| 5,019,151 | 5/1991 | Wada et al. .................. 544/316 |
| 5,085,686 | 2/1992 | Vogelbacher .................. 544/316 |
| 5,100,458 | 3/1992 | Eicken et al. .................. 71/92 |
| 5,149,357 | 9/1992 | Dixson et al. .................. 71/92 |

FOREIGN PATENT DOCUMENTS

| | | |
|---|---|---|
| 223406 | 5/1987 | European Pat. Off. . |
| 249708 | 12/1987 | European Pat. Off. . |
| 287072 | 10/1988 | European Pat. Off. . |
| 287079 | 10/1988 | European Pat. Off. . |

Primary Examiner—Cecilia Tsang
Attorney, Agent, or Firm—Keil & Weinkauf

[57] ABSTRACT

Salicyloyl(thio)ether derivatives of the formula I,

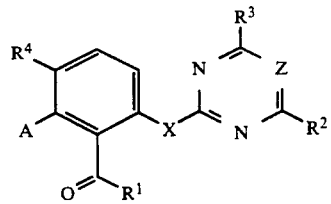

where is oxygen or sulfur and Z is carbon or nitrogen, and the radicals R$^1$ to R$^4$ and A have the meanings given in the disclosure, and processes and intermediates for preparing compounds I.

9 Claims, No Drawings

SALICYLOYL (THIO)ETHER DERIVATIVES, THEIR PREPARATION AND INTERMEDIATES FOR THEIR PREPARATION

The present invention relates to salicyloyl(thio)ether derivatives of the formula I

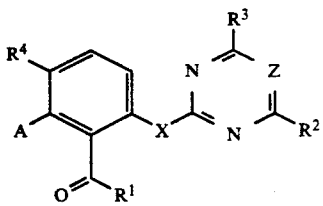

where
$R^1$ is a radical

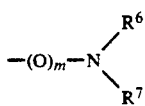

in which m is 0 or 1 and $R^6$ and $R^7$ are each hydrogen; $C_1$-$C_6$-alkyl, $C_3$-$C_6$-alkenyl, $C_3$-$C_6$-alkynyl, where these radicals may each carry from one to five halogen atoms and/or one or two of the following groups: $C_1$-$C_6$-alkoxy, $C_3$-$C_6$-alkenyloxy, $C_3$-$C_6$-alkynyloxy, $C_1$-$C_6$-alkylthio, $C_3$-$C_6$-alkenylthio, $C_3$-$C_6$-alkynylthio, $C_1$-$C_6$-haloalkoxy, cyano, $C_1$-$C_6$-alkylcarbonyl, $C_3$-$C_6$-alkenylcarbonyl, $C_3$-$C_6$-alkynylcarbonyl, $C_1$-$C_6$-alkoxycarbonyl, $C_3$-$C_6$-alkenyloxycarbonyl, $C_3$-$C_6$-alkynyloxycarbonyl, $C_1$-$C_6$-dialkylamino or $C_1$-$C_6$-cycloalkyl; unsubstituted or substituted $C_1$-$C_6$-cycloalkyl; unsubstituted or substituted phenyl;

$R^6$ together with $R^7$ may be an unsubstituted or substituted $C_4$-$C_7$-alkylene chain in which a $CH_2$ group may be replaced with oxygen, sulfur or —NH; a group

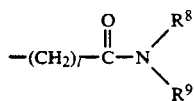

where $R^8$ and $R^9$ are each hydrogen, $C_1$-$C_6$-alkyl, $C_3$-$C_6$-alkenyl or $C_3$-$C_6$-alkynyl and l is 1, 2, 3 or 4; or a group

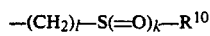

where $R^{10}$ is $C_1$-$C_6$-alkyl, $C_3$-$C_6$-alkenyl or $C_3$-$C_6$-alkynyl, l is 1, 2, 3 or 4 and k is 0, 1 or 2; a radical $OR^5$, where
$R^5$ is an unsubstituted or substituted 5-membered aromatic heterocyclic structure bonded via a nitrogen atom and having from one to four nitrogen atoms in the ring or a radical

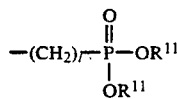

where $R^{11}$ and l have the abovementioned meanings, or a radical

—HN—$SO_2$—$R^{12}$ where $R^{12}$ is $C_1$-$C_6$-alkyl, $C_1$-$C_6$-haloalkyl or phenyl, which in turn may carry from one to four of the following substituents: halogen, nitro, cyano or $C_1$-$C_6$-alkyl; $R^2$ and $R^3$ are each $C_1$-$C_4$-alkyl, $C_1$-$C_4$-haloalkyl, $C_1$-$C_4$-alkoxy, $C_1$-$C_4$-haloalkoxy and/or $C_1$-$C_4$-alkylthio;

X is oxygen or sulfur;

Z is nitrogen or the methine group;

$R^4$ is hydrogen, halogen, nitro, $C_1$-$C_4$-alkyl, cyano or $C_1$-$C_4$-haloalkyl; and A is a 5-membered heteroaromatic structure having from one to four nitrogen atoms or from one to three nitrogen atoms and additionally a sulfur or oxygen atom in the ring, which may carry from one to three halogen atoms and/or from one to three of the following radicals: nitro, cyano, $C_1$-$C_4$-alkyl, $C_1$-$C_4$-alkylthio, $C_1$-$C_4$-haloalkyl or phenyl which is unsubstituted or substituted by from one to three halogen atoms and/or from one to three methyl groups; a benzofused 5-membered heteroaromatic structure which may contain from one to three nitrogen atoms or a nitrogen atom and additionally one oxygen or sulfur atom and may carry one of the following radicals: $C_1$-$C_4$-alkyl, halogen or cyano; a thienyl or furyl radical which may carry from one to three halogen atoms and/or from one to three of the following radicals: $C_1$-$C_4$-alkyl, $C_1$- or $C_2$-haloalkyl, unsubstituted or substituted phenyl or nitro; a benzothienyl or benzofuryl radical which may carry one halogen atom and/or one of the following radicals: $C_1$-$C_4$-alkyl, $C_1$- or $C_2$-haloalkyl or nitro; pyridyl which may carry from one to three halogen atoms and/or from one to three of the following radicals: $C_1$-$C_4$-alkyl, $C_1$- or $C_2$-haloalkyl, unsubstituted or substituted phenyl or nitro; a naphthyl or quinolyl radical, each of which may carry up to three halogen atoms and/or up to three of the following radicals: $C_1$-$C_4$-alkyl or $C_1$- or $C_2$-haloalkyl, the expression unsubstituted or substituted in the abovementioned cases meaning that the corresponding groups may carry one or more of the following substituents: halogen, nitro, cyano, $C_1$-$C_6$-alkyl, $C_1$-$C_6$-haloalkyl, $C_1$-$C_6$-alkoxy or $C_1$-$C_6$-alkylthio.

The literature (EP-A 223 406, EP-A 249 708, EP-A 426 476, EP-A 287 072, EP-A 287 079, EP-A 346 789 and EP-A 402 751) describes herbicidal, substituted salicyclic acids and sulfur analogs thereof. However, their action is not always satisfactory.

It is an object of the present invention to provide novel salicylic acid derivatives or sulfur analogs thereof having improved herbicidal properties or other properties desirable in crop protection, such as growth-regulating or fungicidal activity.

We have found that this object is achieved by the compounds of the formula I which are defined at the outset. We have also found processes for the preparation of the compounds I and methods for controlling undesirable plant growth with the compounds I. We have furthermore found that salicylic acid derivatives of the general formula I defined above have excellent plant growth-regulating properties and in addition possess fungicidal and nitrification-inhibiting activity. The novel salicylic acid derivatives II' were found as intermediates for the preparation of the compounds I.

Compounds of the formula I are obtained, for example, by reacting a correspondingly substituted salicylic acid derivative of the formula II, which is known in specific cases or can be prepared by conventional methods, starting from known intermediates, with a corresponding compound of the formula III in the presence of a base.

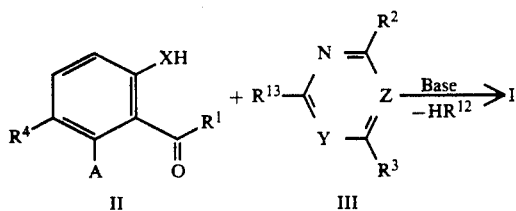

In the formula III, $R^{13}$ is a conventional nucleofugic leaving group, for example halogen, such as chlorine, bromine, iodine, arylsulfonyl or alkylsulfonyl, such as toluenesulfonyl or methylsulfonyl, or another equivalent leaving group. Compounds of the formula III having a reactive substituent $R^{12}$ are known or can readily be obtained with the general technical knowledge. Suitable bases are alkali metal or alkaline earth metal hydrides, such as NaH or CaH$_2$, alkali metal hydroxides, such as NaOH or KOH, alkali metal alcoholates, such as potassium tertbutylate, alkali metal carbonates, such as Na$_2$CO$_3$ or K$_2$CO$_3$, alkali metal amides, such as NaNH$_2$ or lithiumdiisopropylamide, or tertiary amines. When an inorganic base is used, a phase transfer catalyst may be added if it promotes the conversion.

Compounds of the formula I can also be prepared by starting from the corresponding carboxylic acids, i.e. compounds of the formula I in which $R^1$ is hydroxyl, and first converting them in a conventional manner into an activated form, such as a halide or imidazolide, and then reacting this with the corresponding hydroxy compound. These two steps can also be simplified, for example, by allowing the carboxylic acid to act on the hydroxy compound in the presence of a water-eliminating agent, such as a carbodiimide.

Where X is oxygen and A is a heteroaromatic structure bonded via a carbon atom, the intermediates of the formula III can be synthesized according to the following scheme from a 1,3-dicarbonyl compound IV (where $R^5$ is unsubstituted or phenyl-substituted C$_1$-C$_{10}$-alkyl, in particular C$_1$-C$_4$-alkyl) and an α,β-unsaturated ketone V:

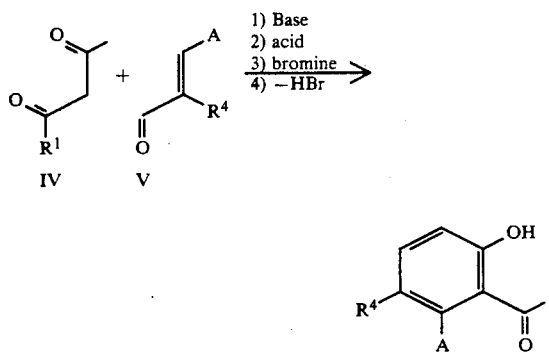

(A is a heteroaromatic or aromatic structure bonded via a carbon atom)

The compounds IV and V are generally known or can be readily prepared by the conventional methods. The abovementioned compounds can be used as the base. Suitable acids are strong acids, for example hydrochloric acid, hydrobromic acid, tetrafluoboric acid, toluenesulfonic acid or trifluoroacetic acid. The elimination of hydrogen bromide may be carried out thermally or in the presence of a base, for example of an organic amine.

If, in the formula II, A is a heteroaromatic structure bonded via a nitrogen atom and X is oxygen, this intermediate may be synthesized according to the following scheme:

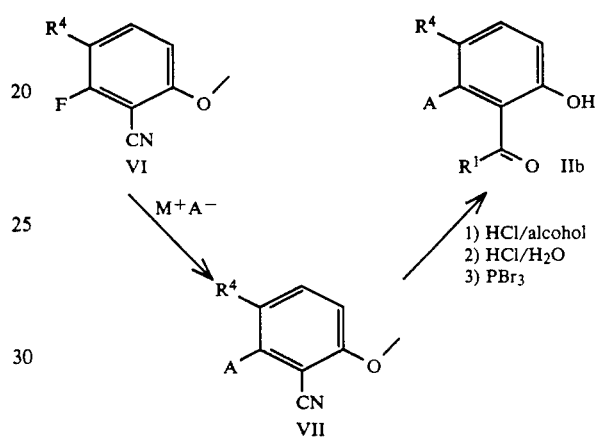

(A is a heteroaromatic structure bonded via N)

$M^+A^-$ is the particular alkali metal azolide. C$_1$-C$_4$-Alkyl alcohols are particularly suitable alcohols for the cleavage of the nitrile VII.

The intermediates of the formula II which are prepared as described above are usually obtained as alkyl esters. These can be hydrolyzed by the known methods to give the carboxylic acids. The latter can be converted by methods known from the literature into various esters which are required for the preparation of the active ingredients of the formula I as claimed in claim 1.

With regard to the herbicidal and plant growth-regulating activity, preferred compounds I are those in which the substituents have the following meanings: $R^1$ is a radical

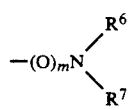

where m is 0 or 1 and $R^6$ and $R^7$ are each hydrogen; alkyl, in particular methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 1-methylhexyl, 2-methylhexyl, 3-methylhexyl, 4-methylhexyl, 5-methylhexyl, 1-ethylpentyl, 2-ethylpentyl, 1-propylbutyl or octyl;

alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-3-butenyl, 1,2-dimethyl-3-butenyl, 1,3-dimethyl-2-buteny1,1,3-dimethyl-3-butenyl, 2,2-dimethyl-3-butenyl, 2,3-dimethyl-2-butenyl, 2,3-dimethyl-3-butenyl, 1-ethyl-2-butenyl, 2-ethyl-2-butenyl, 1-ethyl-3-butenyl, 2-ethyl-3-butenyl, 1,1,2-trimethyl-2-propenyl, 1-ethyl-1-methyl-2-propenyl, 1-ethyl-2-methyl-2-propenyl, in particular 2-propenyl, 2-butenyl, alkynyl, such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, preferably 2-propynyl, 2-butynyl, 1-methyl-2-propynyl or 1-methyl-2-butynyl, in particular 2-propyl or 1-methyl-2-propynyl.

The abovementioned alkyl, alkenyl or alkynyl groups may each carry from one to five halogen atoms, preferably fluorine and chlorine and/or one or two of the following radicals: cyano; alkoxy of one to four carbon atoms, in particular methoxy, ethoxy, propoxy, 1-methylethoxy, butoxy, 1-methylpropoxy, 2-methylpropoxy or 1,1-dimethylethoxy, preferably methoxy, ethoxy or 1-methylethoxy; alkenyloxy of one to four carbon atoms, in particular ethenyloxy, propenyloxy, 1-methylethenyloxy, butenyloxy, 1-methylpropenyloxy, 2-methylpropenyloxy or 1,1-dimethylethenyloxy, preferably ethenyloxy or 1-methylethenyloxy; alkynyloxy of one to four carbon atoms, in particular ethynyloxy, propynyloxy, 1-methylethynyloxy, butynyloxy, 1-methylpropynyloxy, 2-methylpropynyloxy or 1,1-dimethylethynyloxy, preferably ethynyloxy or 1-methylethynyloxy; alkylthio of one to four carbon atoms, in particular methylthio, ethylthio, propylthio, 1-methylethylthio, butylthio, 1-methylpropylthio, 2-methylpropylthio or 1,1-dimethylethylthio, preferably methylthio, ethylthio or 1-methylethylthio; alkenylthio of one to four carbon atoms, in particular ethenylthio, propenylthio, 1-methylethenylthio, butenylthio, 1-methylpropenylthio, 2-methylpropenylthio or 1,1-dimethylethenylthio, preferably ethenylthio or 1-methylethenylthio; alkynylthio of one to four carbon atoms, in particular ethynylthio, propynylthio, 1-methylethynylthio, butynylthio, 1-methylpropynylthio, 2-methylpropynylthio or 1,1-dimethylethynylthio, preferably ethynylthio or 1-methylethynylthio; haloalkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy,2-chloro-1,1,2-trifluoroethoxy or pentafluoroethoxy, in particular difluoromethoxy or trifluoromethoxy; alkylcarbonyl, in particular methylcarbonyl, ethylcarbonyl, propylcarbonyl, 1-methylethylcarbonyl, butylcarbonyl, 1-methylpropylcarbonyl, 1,1-dimethylethylcarbonyl, pentylcarbonyl, 2-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl; alkoxycarbonyl, such as methoxycarbonyl, ethoxycarbonyl, propoxycarbonyl, 1-methylethoxycarbonyl, butoxycarbonyl, 1-methylpropoxycarbonyl, 2-methylpropoxycarbonyl, 1,1-dimethylpropoxycarbonyl, n-pentyloxycarbony, 1-methylbutoxycarbonyl, 2-methylbutoxycarbonyl, 3-methylbutoxycarbonyl, 1,2-dimethylpropoxycarbonyl, 1,1-dimethylpropoxycarbonyl, 2,2-dimethylpropoxycarbonyl, 1-ethylpropoxycarbonyl, 1-hexyloxycarbonyl, 1-methylpentenyloxycarbonyl, 2-methylpentenyloxycarbonyl, 3-methylpentenyloxycarbonyl, 4-methylpentenyloxycarbonyl, 1,2-dimethylbutoxycarbonyl, 1,3-dimethylbutoxycarbonyl, 2,3-dimethylbutoxycarbonyl, 1 -dimethylbutoxycarbonyl, 1,1-dimethylbutoxycarbonyl, 2,2-dimethylbutoxycarbonyl, 3,3-dimethylbutoxycarbonyl, 1,1,2-trimethylpropoxycarbonyl, 1,2,2-trimethylpropoxycarbonyl, 1-ethylbutoxycarbonyl, 2-ethylbutoxycarbonyl, 1-ethyl-2-methylpropoxycarbonyl, n-heptyloxycarbonyl, 1-methylhexyloxycarbonyl, 2-methylhexyloxycarbonyl, 3-methylhexyloxycarbonyl, 4-methylhexyloxycarbonyl, 5-methylhexyloxycarbonyl, 1-ethylpentenyloxycarbonyl, 1-propylbutoxycarbonyl or octyloxycarbonyl, in particular methoxycarbonyl, ethoxycarbonyl, 1-methylethoxycarbonyl or 1-methylpropoxycarbonyl; cycloalkyl, such as cyclopropyl, cyclobutyl, cyclopentyl, cyclohexyl or cycloheptyl; dialkylamino, such as dimethylamino, diethylamino, dipropylamino, di-1-methylethyl, dibutylamino, di-1-methylpropylamino, di-2-methylpropylamino, di-1,1-methylethylamino, ethylmethylamino, propylmethylamino, 1-methylethylmethylamino or butylmethylamino; phenyl, phenoxy or phenylcarbonyl, where these aromatic radicals in turn may carry from one to five halogen atoms as stated above, in particular fluorine, chlorine and bromine, and/or from one to three of the following radicals: alkyl, haloalkyl, alkoxy and/or alkylthio, each of one to four carbon atoms, as stated above in general and in particular; $C_2$–$C_{12}$-cycloalkyl, in particular $C_3$–$C_6$-cycloalkyl, such as cyclopropyl, cyclobutyl, cyclopentyl or cyclohexyl, which is unsubstituted or substituted by one to three $C_1$–$C_4$-alkyl radicals; phenyl which is unsubstituted or monosubstituted to trisubstituted by $C_1$–$C_4$-alkyl or $C_1$–$C_4$-alkoxy, such as methyl, ethyl, propyl, butyl, methoxy or ethoxy or phenyl which is substituted by one to five halogen atoms, e.g. chlorine or fluorine;

$R^6$ and $R^7$ together form an alkylene group which is closed to form a ring, or together form an alkylene group which has a hetero atom and is closed to form a ring, the ring preferably having from five to seven members and the hetero atom being oxygen, nitrogen or sulfur, and the ring thus formed carries one or more of the radicals stated under unsubstituted or substituted.

The following radicals may be mentioned in particular for the group —NR⁶R⁷: dimethylamino, tert-butylamino, cyclohexylamino, 1-cyano-1-cyclohexylamino, isopropylamino, sec-butylamino, methylamino, diethylamino, 1-pyrrolidinyl, 1-piperidyl, 4-morpholinyl, phenylamino, methylphenylamino, methoxymethylamino, bis(methoxymethyl)-amino or methylthiomethylamino; a radical

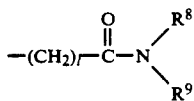

where l is from 1 to 4, preferably 1 or 2, and R⁸ and R⁹ are each alkyl, alkenyl or alkynyl as stated above; a radical

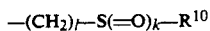

where l is from 1 to 4, preferably 1 or 2, and R¹⁰ is alkyl, alkenyl or alkynyl as stated above; a radical OR⁵, where R¹ is a 5-membered hetaryl which has from one to four nitrogen atoms in the ring, is bonded via a nitrogen atom and may carry from one to four of the radicals stated under unsubstituted or substituted. Particular examples are 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 4-bromo-1-pyrazolyl, 4-iodo-1-pyrazolyl, 1-imidazolyl, 1-benzoimidazolyl, 1,2,4-triazol-1-yl, 3-methyl-1,2,4-triazol-1-yl, 5-methyl-1,2,4-triazol-1-yl or 1-benzotriazolyl, or a group

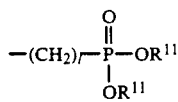

where l is from 1 to 4, preferably 1 or 2, and R¹¹ is alkyl, alkenyl or alkynyl as stated for R⁶ and R⁷, a radical

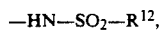

where R¹² has the following meanings: C₁-C₆-alkyl which may carry from one to four of the following substituents: halogen, nitro, cyano or C₁-C₆-alkyl, particular examples being methyl, cyanomethyl, ethyl, 2-nitroethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl or 1-ethyl-2-methylpropyl; phenyl which may carry from one to four of the following substituents: halogen, nitro, cyano or C₁-C₆-alkyl, particular examples being 2-fluorophenyl, 3-fluorophenyl, 4-fluorophenyl, 2,6-difluorophenyl, 2,4-difluorophenyl, 2,3-difluorophenyl, 2-fluoro-4-trifluoromethylphenyl, 2-chlorophenyl, 3-chlorophenyl, 2-bromophenyl, 2-iodophenyl, 2-chloro-6-fluorophenyl, 2,4-dichlorophenyl, 2,6-dichlorophenyl, 3,5-dichlorophenyl, 2-chloro-4-fluorophenyl, 2-chloro-6-methylphenyl, 2,3,5-trichlorophenyl, 2-methylphenyl, 3-methylphenyl, 4-methylphenyl, 2,6-dimethylphenyl, 2,4-dimethylphenyl, 3,5-dimethylphenyl, 2,4,6-trimethylphenyl, 2-chloro-4-methylphenyl, 2-trifluoromethylphenyl, 3-trifluoromethylphenyl, 2-cyanophenyl, 3-cyanophenyl, 4-cyanophenyl, 2-nitrophenyl, 3-nitrophenyl or 4-nitrophenyl; R² and R³ are each in general and in particular the alkyl, haloalkyl, alkoxy, haloalkoxy and/or alkylthio groups stated for R⁶ and R⁷, each of one to four carbon atoms, in particular methyl, trifluoromethyl, methoxy, difluoromethoxy or methylthio; R⁴ is hydrogen; halogen, in particular fluorine or chlorine, cyano; alkyl of one to four, in particular one to three, carbon atoms which is monosubstituted to penta-substituted by halogen, in particular fluorine or chlorine. Examples are methyl, ethyl, n-propyl, isopropyl, trichloromethyl and trifluoromethyl.

A is unsubstituted or substituted 5-membered hetaryl having from one to four nitrogen atoms, such as pyrrolyl, pyrazolyl, imidazolyl, 1,2,3-triazolyl, 1,2,4-triazolyl or tetrazolyl, or having one or two nitrogen atoms and in addition one sulfur or oxygen atom, such as isoxazolyl, oxazoly, thiazolyl or thiadiazolyl; examples of hetaryl radicals are the following: pyrrol-1-yl, 2-methylpyrrol-1-yl, 3-methylpyrrol-1-yl, 1-methylpyrrol-2-yl, 1-methylpyrrol-3-yl, pyrazol-1-yl, 4-methylpyrazol-1-yl, 3,5-dimethylpyrazol-1-yl, 3,4,5-trimethylpyrazol-1-yl, 4-chloropyrazol-1-yl, 4-phenylpyrazolyl-1-yl, 4-nitropyrazol-1-yl, imidazol-1-yl, 4,5-dimethylimidazol-1-yl, 2-methyl-4,5-dichloroimidazol-1-yl, 4-nitroimidazol-1-yl, 5-nitroimidazol-1-yl, 1,2,4-triazol-1-yl, 3(5)-methyl-1,2,4-triazol-1-yl, 1,2,3-triazol-1-yl, 4,5-dimethyl-1,2,3-triazol-1-yl, 1,2,3,4-tetrazol-1-yl, 1-methylpyrazol-4-yl, 1-phenylpyrazol-4-yl, 1,3,5-trimethylpyrazol-4-yl, 1-methylpyrazol-5-yl, 1-phenylpyrazol-5-yl, 1-methylpyrazol-3-yl, 1-phenylpyrazol-3-yl, 1-methylimidazol-2-yl, 1-methylimidazol-5-yl, 1-phenylimidazol-5-yl, 1-phenyl-1,2,3-triazol-4-yl, isoxazol-5-yl, isoxazol-4-yl, 4-methylisoxazol-5-yl, 3-isopropylisoxazol-5-yl, 3-phenylisoxazol-5-yl, oxazol-2-yl, 2-methyloxazol-4-yl, thiazol-4-yl, 4-methylthiazol-2-yl, 4-methylthiazol-5-yl, 2-phenylthiazol-5-yl and 4-phenylthiazol-2-yl; unsubstituted or substituted benzofused hetaryl having from one to three nitrogen atoms or one nitrogen atom and one oxygen or sulfur atom in the ring, for example indolyl, indazolyl, benzotriazolyl, benzoxazolyl, benzoisoxazolyl or benzothiazolyl; unsubstituted or substituted thienyl radicals or benzothienyl radicals are, for example, 2-thienyl, 3-thienyl, 2-chloro-5-thienyl, 4-bromo-2-thienyl,2-nitro-5-thienyl, 2-benzothienyl and 3-benzothienyl; and unsubstituted or substituted naphthyl or quinolyl radicals are, for example, 1-naphthyl, 2-naphthyl, 2-chloro-1-naphthyl, 6-chloro-1-naphthyl,2,6-dichloro-1-naphthyl, 2-methyl-6-chloro-1-naphthyl, 2-quinolyl, 4-quinolyl, 6-quinolyl, 8-quinolyl and 6-methyl-2-quinolyl.

If a radical is referred to as unsubstituted or substituted, it may carry one or more, in particular from one to three, of the following substituents: halogen, in particular chlorine or bromine, nitro, cyano or alkyl, haloalkyl, alkoxy or alkylthio as stated for R⁶ and R⁷.

Particularly preferred compounds of the formula I are those in which

R² and R³ are each methoxy, methyl, difluoromethoxy or chlorine,

R⁴ is hydrogen or methyl and

R⁶ and R⁷ are each hydrogen, methyl or a C₄- or C₅-alkylene chain and in which X is oxygen, Y is nitrogen and Z is a methine group and A has the meanings stated in the claim.

The structures given in the tables below describe particularly preferred active ingredients of the formula I.

TABLE 1

Compounds I in which R¹ is a radical ONR⁶R⁷

| R⁶ | R⁷ | X | Z | A | Phys. data m.p. [°C.] |
|---|---|---|---|---|---|
| CH₃ | CH₃ | O | N | 1-Pyrrolyl | |
| CH₃ | CH₃ | O | CH | 1-Pyrrolyl | |
| H | H | O | CH | 1-Pyrrolyl | |
| CH₃ | H | O | CH | 1-Pyrrolyl | |
| CH₃ | C₂H₅ | O | CH | 1-Pyrrolyl | |
| C₂H₅ | C₂H₅ | O | CH | 1-Pyrrolyl | |
| H | n-C₃H₇ | O | CH | 1-Pyrrolyl | |
| n-C₃H₇ | n-C₃H₇ | O | CH | 1-Pyrrolyl | |
| H | i-C₃H₇ | O | CH | 1-Pyrrolyl | |
| H | n-C₄H₉ | O | CH | 1-Pyrrolyl | |
| H | t-C₄H₉ | O | CH | 1-Pyrrolyl | |
| CH₂CH=CH₂ | CH₂CH=CH₂ | O | CH | 1-Pyrrolyl | |
| CH₂C≡CH | CH₂C≡CH | O | CH | 1-Pyrrolyl | |
| CH₂CH₂Cl | CH₂CH₂Cl | O | CH | 1-Pyrrolyl | |
| (CH₂)₂OCH₃ | (CH₂)₂OCH₃ | O | CH | 1-Pyrrolyl | |
| CH₂CO₂CH₃ | CH₂CO₂CH₃ | O | CH | 1-Pyrrolyl | |
| CH₃ | CH₂CO₂CH₃ | O | CH | 1-Pyrrolyl | |
| CH₂CN | CH₂CN | O | CH | 1-Pyrrolyl | |
| CH₂CH₂CN | CH₂CH₂CN | O | CH | 1-Pyrrolyl | |
| H | Cyclohexyl | O | CH | 1-Pyrrolyl | |
| H | CH₂C₆H₅ | O | CH | 1-Pyrrolyl | |
| CH₂C₆H₅ | CH₂C₆H₅ | O | CH | 1-Pyrrolyl | |
| CH₃ | C₆H₅ | O | CH | 1-Pyrrolyl | |
| (CH₂)₂SCH₃ | (CH₂)₂SCH₃ | O | CH | 1-Pyrrolyl | |
| —CH₂CH₂CH₂CH₂— | | O | CH | 1-Pyrrolyl | |
| —CH₂CH₂CH₂CH₂CH₂— | | O | CH | 1-Pyrrolyl | |
| —CH₂CH₂CH₂CH₂CH₂CH₂— | | O | CH | 1-Pyrrolyl | |
| —CH₂CH₂OCH₂CH₂— | | O | CH | 1-Pyrrolyl | |
| CH₃ | CH₃ | S | CH | 1-Pyrrolyl | |
| CH₃ | CH₃ | O | N | 1-Methyl-pyrrol-2-yl | |
| CH₃ | CH₃ | O | CH | 1-Methyl-pyrrol-2-yl | |
| CH₃ | CH₃ | S | CH | 1-Methyl-pyrrol-2-yl | |
| CH₃ | CH₃ | O | N | 1-Methyl-pyrrol-3-yl | |
| CH₃ | CH₃ | O | CH | 1-Methyl-pyrrol-3-yl | |
| CH₃ | CH₃ | S | CH | 1-Methyl-pyrrol-3-yl | |
| CH₃ | CH₃ | O | CH | 1-Indolyl | |
| CH₃ | CH₃ | O | CH | 1-Methyl-indol-2-yl | |
| CH₃ | CH₃ | O | CH | 1-Methyl-indol-3-yl | |
| CH₃ | CH₃ | O | CH | 3-Methyl-indol-1-yl | |
| CH₃ | CH₃ | O | CH | 3,5-Dimethyl-pyrrol-1-yl | |
| CH₃ | CH₃ | O | CH | 3-Methylpyrrol-1-yl | |
| CH₃ | CH₃ | O | CH | 4-Methylpyrrol-1-yl | |
| CH₃ | CH₃ | O | CH | 4-chloropyrrol-1-yl | |
| CH₃ | CH₃ | O | CH | 4-bromopyrrol-1-yl | |
| CH₃ | CH₃ | O | CH | 4-Phenylpyrrol-1-yl | |
| CH₃ | CH₃ | O | CH | 3,4,5-Trimethyl-pyrrol-1-yl | |
| CH₃ | CH₃ | O | CH | 4-chloro-3,5-dimethyl-pyrrol-1-yl | |
| CH₃ | CH₃ | O | CH | 4-Isopropylpyrrol-1-yl | |
| CH₃ | CH₃ | O | CH | 3-Phenylpyrrol-1-yl | |
| CH₃ | CH₃ | O | CH | 3-Methyl-5-phenyl-pyrrol-1-yl | |
| CH₃ | CH₃ | O | CH | 3,5-Bistrifluoromethyl-pyrrol-1-yl | |
| CH₃ | CH₃ | O | CH | 4-Nitropyrrol-1-yl | |
| CH₃ | CH₃ | O | CH | 1-Phenylpyrrol-3-yl | |
| CH₃ | CH₃ | O | CH | 1,3,5-Trimethyl-pyrrol-4-yl | |
| CH₃ | CH₃ | O | CH | 1-Phenylpyrrol-2-yl | |
| CH₃ | CH₃ | O | CH | 1-Phenylpyrrol-3-yl | |
| CH₃ | CH₃ | O | CH | 1,4-Dimethylpyrrol-3-yl | |
| CH₃ | CH₃ | O | CH | 5-Methyl-1-phenyl-pyrrol-3-yl | |
| CH₃ | CH₃ | O | CH | 1,5-Dimethylpyrrol-3-yl | |
| CH₃ | CH₃ | O | CH | 1,3-Dimethylpyrrol-4-yl | |
| CH₃ | CH₃ | O | CH | 1,5-Dimethylpyrrol-3-yl | |
| CH₃ | CH₃ | O | CH | 3-Methyl-1-phenyl-pyrrol-4-yl | |
| CH₃ | CH₃ | O | CH | 5-Methyl-1-phenyl-pyrrol-2-yl | |
| CH₃ | CH₃ | O | CH | 3,5-Dimethyl-1-phenyl-pyrrol-4-yl | |

TABLE 1-continued

Compounds I in which R¹ is a radical ONR⁶R⁷

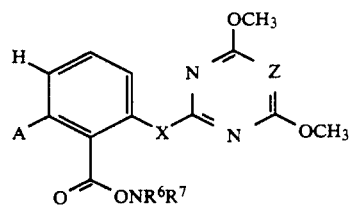

| R⁶ | R⁷ | X | Z | A | Phys. data m.p. [°C.] |
|---|---|---|---|---|---|
| CH₃ | CH₃ | O | CH | 3-Methyl-1-phenyl-pyrrol-5-yl | |
| CH₃ | CH₃ | O | CH | 1,4-Dimethylpyrrol-5-yl | |
| CH₃ | CH₃ | O | CH | 1,3-Dimethylpyrrol-5-yl | |
| CH₃ | CH₃ | O | N | 2-Thienyl | |
| CH₃ | CH₃ | O | CH | 2-Thienyl | |
| H | H | O | CH | 2-Thienyl | |
| CH₃ | H | O | CH | 2-Thienyl | |
| CH₃ | C₂H₅ | O | CH | 2-Thienyl | |
| C₂H₅ | C₂H₅ | O | CH | 2-Thienyl | |
| H | n-C₃H₇ | O | CH | 2-Thienyl | |
| n-C₃H₇ | n-C₃H₇ | O | CH | 2-Thienyl | |
| H | i-C₃H₇ | O | CH | 2-Thienyl | |
| H | n-C₄H₉ | O | CH | 2-Thienyl | |
| H | t-C₄H₉ | O | CH | 2-Thienyl | |
| CH₂CH=CH₂ | CH₂CH=CH₂ | O | CH | 2-Thienyl | |
| CH₂C≡CH | CH₂C≡CH | O | CH | 2-Thienyl | |
| CH₂CH₂Cl | CH₂CH₂Cl | O | CH | 2-Thienyl | |
| (CH₂)₂OCH₃ | (CH₂)₂OCH₃ | O | CH | 2-Thienyl | |
| CH₂CO₂CH₃ | CH₂CO₂CH₃ | O | CH | 2-Thienyl | |
| CH₃ | CH₂CO₂CH₃ | O | CH | 2-Thienyl | |
| CH₂CN | CH₂CN | O | CH | 2-Thienyl | |
| CH₂CH₂CN | CH₂CH₂CN | O | CH | 2-Thienyl | |
| H | Cyclohexyl | O | CH | 2-Thienyl | |
| H | CH₂C₆H₅ | O | CH | 2-Thienyl | |
| CH₂C₆H₅ | CH₂C₆H₅ | O | CH | 2-Thienyl | |
| CH₃ | C₆H₅ | O | CH | 2-Thienyl | |
| (CH₂)₂SCH₃ | (CH₂)₂SCH₃ | O | CH | 2-Thienyl | |
| —CH₂CH₂CH₂CH₂— | | O | CH | 2-Thienyl | |
| —CH₂CH₂CH₂CH₂CH₂— | | O | CH | 2-Thienyl | |
| —CH₂CH₂CH₂CH₂CH₂CH₂— | | O | CH | 2-Thienyl | |
| —CH₂CH₂OCH₂CH₂— | | O | CH | 2-Thienyl | |
| CH₃ | CH₃ | S | CH | 2-Thienyl | |
| CH₃ | CH₃ | O | N | 3-Thienyl | |
| CH₃ | CH₃ | O | CH | 3-Thienyl | |
| H | H | O | CH | 3-Thienyl | |
| CH₃ | H | O | CH | 3-Thienyl | |
| CH₃ | C₂H₅ | O | CH | 3-Thienyl | |
| C₂H₅ | C₂H₅ | O | CH | 3-Thienyl | |
| H | n-C₃H₇ | O | CH | 3-Thienyl | |
| n-C₃H₇ | n-C₃H₇ | O | CH | 3-Thienyl | |
| H | i-C₃H₇ | O | CH | 3-Thienyl | |
| H | n-C₄H₉ | O | CH | 3-Thienyl | |
| H | t-C₄H₉ | O | CH | 3-Thienyl | |
| CH₂CH=CH₂ | CH₂CH=CH₂ | O | CH | 3-Thienyl | |
| CH₂C≡CH | CH₂C≡CH | O | CH | 3-Thienyl | |
| CH₂CH₂Cl | CH₂CH₂Cl | O | CH | 3-Thienyl | |
| (CH₂)₂OCH₃ | (CH₂)₂OCH₃ | O | CH | 3-Thienyl | |
| CH₂CO₂CH₃ | CH₂CO₂CH₃ | O | CH | 3-Thienyl | |
| CH₃ | CH₂CO₂CH₃ | O | CH | 3-Thienyl | |
| CH₂CN | CH₂CN | O | CH | 3-Thienyl | |
| CH₂CH₂CN | CH₂CH₂CN | O | CH | 3-Thienyl | |
| H | Cyclohexyl | O | CH | 3-Thienyl | |
| H | CH₂C₆H₅ | O | CH | 3-Thienyl | |
| CH₂C₆H₅ | CH₂C₆H₅ | O | CH | 3-Thienyl | |
| CH₃ | C₆H₅ | O | CH | 3-Thienyl | |
| (CH₂)₂SCH₃ | (CH₂)₂SCH₃ | O | CH | 3-Thienyl | |
| —CH₂CH₂CH₂CH₂— | | O | CH | 3-Thienyl | |
| —CH₂CH₂CH₂CH₂CH₂— | | O | CH | 3-Thienyl | |
| —CH₂CH₂CH₂CH₂CH₂CH₂— | | O | CH | 3-Thienyl | |
| —CH₂CH₂OCH₂CH₂— | | O | CH | 3-Thienyl | |
| CH₃ | CH₃ | S | CH | 3-Thienyl | |
| CH₃ | CH₃ | O | CH | 2,3-Dichloro-4-thienyl | |
| CH₃ | CH₃ | O | CH | 2,5-Dichloro-3-thienyl | |
| CH₃ | CH₃ | O | CH | 2-bromo-5-thienyl | |
| CH₃ | CH₃ | O | CH | 4-bromo-2-thienyl | |
| CH₃ | CH₃ | O | CH | 3-Methyl-2-thienyl | |
| CH₃ | CH₃ | O | CH | 2-chloro-5-thienyl | |

TABLE 1-continued

Compounds I in which $R^1$ is a radical $ONR^6R^7$

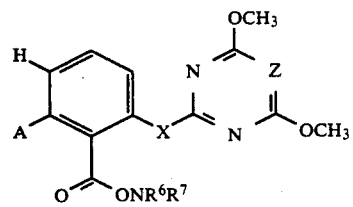

| $R^6$ | $R^7$ | X | Z | A | Phys. data m.p. [°C.] |
|---|---|---|---|---|---|
| CH₃ | CH₃ | O | CH | 2-Methyl-5-thienyl | |
| CH₃ | CH₃ | O | CH | 2-Nitro-5-thienyl | |
| CH₃ | CH₃ | O | N | Benzthien-2-yl | |
| CH₃ | CH₃ | O | CH | Benzthien-2-yl | |
| CH₃ | CH₃ | S | CH | Benzthien-2-yl | |
| CH₃ | CH₃ | O | N | Benzthien-3-yl | |
| CH₃ | CH₃ | O | CH | Benzthien-3-yl | |
| CH₃ | CH₃ | S | CH | Benzthien-3-yl | |
| CH₃ | CH₃ | O | N | 2-Furanyl | |
| CH₃ | CH₃ | O | CH | 2-Furanyl | |
| CH₃ | CH₃ | S | CH | 2-Furanyl | |
| H | H | O | CH | 2-Furanyl | |
| CH₃ | H | O | CH | 2-Furanyl | |
| CH₃ | C₂H₅ | O | CH | 2-Furanyl | |
| C₂H₅ | C₂H₅ | O | CH | 2-Furanyl | |
| H | n-C₃H₇ | O | CH | 2-Furanyl | |
| n-C₃H₇ | n-C₃H₇ | O | CH | 2-Furanyl | |
| H | i-C₃H₇ | O | CH | 2-Furanyl | |
| H | n-C₄H₉ | O | CH | 2-Furanyl | |
| H | t-C₄H₉ | O | CH | 2-Furanyl | |
| CH₂CH=CH₂ | CH₂CH=CH₂ | O | CH | 2-Furanyl | |
| CH₂C≡CH | CH₂C≡CH | O | CH | 2-Furanyl | |
| CH₂CH₂Cl | CH₂CH₂Cl | O | CH | 2-Furanyl | |
| (CH₂)₂OCH₃ | (CH₂)₂OCH₃ | O | CH | 2-Furanyl | |
| CH₂CO₂CH₃ | CH₂CO₂CH₃ | O | CH | 2-Furanyl | |
| CH₃ | CH₂CO₂CH₃ | O | CH | 2-Furanyl | |
| CH₂CN | CH₂CN | O | CH | 2-Furanyl | |
| CH₂CH₂CN | CH₂CH₂CN | O | CH | 2-Furanyl | |
| H | Cyclohexyl | O | CH | 2-Furanyl | |
| H | CH₂C₆H₅ | O | CH | 2-Furanyl | |
| CH₂C₆H₅ | CH₂C₆H₅ | O | CH | 2-Furanyl | |
| CH₃ | C₆H₅ | O | CH | 2-Furanyl | |
| (CH₂)₂SCH₃ | (CH₂)₂SCH₃ | O | CH | 2-Furanyl | |
| —CH₂CH₂CH₂CH₂— | | O | CH | 2-Furanyl | |
| —CH₂CH₂CH₂CH₂CH₂— | | O | CH | 2-Furanyl | |
| —CH₂CH₂CH₂CH₂CH₂CH₂— | | O | CH | 2-Furanyl | |
| —CH₂CH₂OCH₂CH₂— | | O | CH | 2-Furanyl | |
| CH₃ | CH₃ | O | N | 3-Furanyl | |
| CH₃ | CH₃ | O | CH | 3-Furanyl | |
| CH₃ | CH₃ | S | CH | 3-Furanyl | |
| H | H | O | CH | 3-Furanyl | |
| CH₃ | H | O | CH | 3-Furanyl | |
| CH₃ | C₂H₅ | O | CH | 3-Furanyl | |
| C₂H₅ | C₂H₅ | O | CH | 3-Furanyl | |
| H | n-C₃H₇ | O | CH | 3-Furanyl | |
| n-C₃H₇ | n-C₃H₇ | O | CH | 3-Furanyl | |
| H | i-C₃H₇ | O | CH | 3-Furanyl | |
| H | n-C₄H₉ | O | CH | 3-Furanyl | |
| H | t-C₄H₉ | O | CH | 3-Furanyl | |
| CH₂CH=CH₂ | CH₂CH=CH₂ | O | CH | 3-Furanyl | |
| CH₂C≡CH | CH₂C≡CH | O | CH | 3-Furanyl | |
| CH₂CH₂Cl | CH₂CH₂Cl | O | CH | 3-Furanyl | |
| (CH₂)₂OCH₃ | (CH₂)₂OCH₃ | O | CH | 3-Furanyl | |
| CH₂CO₂CH₃ | CH₂CO₂CH₃ | O | CH | 3-Furanyl | |
| CH₃ | CH₂CO₂CH₃ | O | CH | 3-Furanyl | |
| CH₂CN | CH₂CN | O | CH | 3-Furanyl | |
| CH₂CH₂CN | CH₂CH₂CN | O | CH | 3-Furanyl | |
| H | Cyclohexyl | O | CH | 3-Furanyl | |
| H | CH₂C₆H₅ | O | CH | 3-Furanyl | |
| CH₂C₆H₅ | CH₂C₆H₅ | O | CH | 3-Furanyl | |
| CH₃ | C₆H₅ | O | CH | 3-Furanyl | |
| (CH₂)₂SCH₃ | (CH₂)₂SCH₃ | O | CH | 3-Furanyl | |
| —CH₂CH₂CH₂CH₂— | | O | CH | 3-Furanyl | |
| —CH₂CH₂CH₂CH₂CH₂— | | O | CH | 3-Furanyl | |
| —CH₂CH₂CH₂CH₂CH₂CH₂— | | O | CH | 3-Furanyl | |
| —CH₂CH₂OCH₂CH₂— | | O | CH | 3-Furanyl | |
| CH₃ | CH₃ | O | CH | 2,3-Dichloro-4-furanyl | |

TABLE 1-continued

Compounds I in which R¹ is a radical ONR⁶R⁷

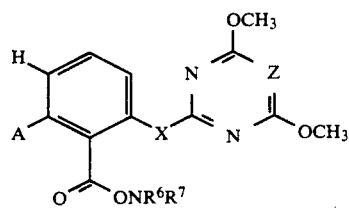

| R⁶ | R⁷ | X | Z | A | Phys. data m.p. [°C.] |
|---|---|---|---|---|---|
| CH₃ | CH₃ | O | CH | 2,5-Dichloro-3-furanyl | |
| CH₃ | CH₃ | O | CH | 2-bromo-5-furanyl | |
| CH₃ | CH₃ | O | CH | 4-bromo-2-furanyl | |
| CH₃ | CH₃ | O | CH | 3-Methyl-2-furanyl | |
| CH₃ | CH₃ | O | CH | 2-chloro-5-furanyl | |
| CH₃ | CH₃ | O | CH | 2-Methyl-5-furanyl | |
| CH₃ | CH₃ | O | CH | 2-Nitro-5-furanyl | |
| CH₃ | CH₃ | O | N | Benzofuran-2-yl | |
| CH₃ | CH₃ | O | CH | Benzofuran-2-yl | |
| CH₃ | CH₃ | S | CH | Benzofuran-2-yl | |
| CH₃ | CH₃ | O | N | Benzofuran-3-yl | |
| CH₃ | CH₃ | O | CH | Benzofuran-3-yl | |
| CH₃ | CH₃ | S | CH | Benzofuran-3-yl | |
| CH₃ | CH₃ | O | N | 1-Pyrazolyl | |
| CH₃ | CH₃ | O | CH | 1-Pyrazolyl | |
| H | H | O | CH | 1-Pyrazolyl | |
| CH₃ | H | O | CH | 1-Pyrazolyl | |
| CH₃ | CH₃ | O | CH | 1-Pyrazolyl | |
| C₂H₅ | C₂H₅ | O | CH | 1-Pyrazolyl | |
| H | n-C₃H₇ | O | CH | 1-Pyrazolyl | |
| n-C₃H₇ | n-C₃H₇ | O | CH | 1-Pyrazolyl | |
| H | i-C₃H₇ | O | CH | 1-Pyrazolyl | |
| H | n-C₄H₉ | O | CH | 1-Pyrazolyl | |
| H | t-C₄H₉ | O | CH | 1-Pyrazolyl | |
| CH₂CH=CH₂ | CH₂CH=CH₂ | O | CH | 1-Pyrazolyl | |
| CH₂C≡CH | CH₂C≡CH | O | CH | 1-Pyrazolyl | |
| CH₂CH₂Cl | CH₂CH₂Cl | O | CH | 1-Pyrazolyl | |
| (CH₂)₂OCH₃ | (CH₂)₂OCH₃ | O | CH | 1-Pyrazolyl | |
| CH₂CO₂CH₃ | CH₂CO₂CH₃ | O | CH | 1-Pyrazolyl | |
| CH₃ | CH₂CO₂CH₃ | O | CH | 1-Pyrazolyl | |
| CH₂CN | CH₂CN | O | CH | 1-Pyrazolyl | |
| CH₂CH₂CN | CH₂CH₂CN | O | CH | 1-Pyrazolyl | |
| H | Cyclohexyl | O | CH | 1-Pyrazolyl | |
| H | CH₂C₆H₅ | O | CH | 1-Pyrazolyl | |
| CH₂C₆H₅ | CH₂C₆H₅ | O | CH | 1-Pyrazolyl | |
| CH₃ | C₆H₅ | O | CH | 1-Pyrazolyl | |
| (CH₂)₂SCH₃ | (CH₂)₂SCH₃ | O | CH | 1-Pyrazolyl | |
| —CH₂CH₂CH₂CH₂— | | O | CH | 1-Pyrazolyl | |
| —CH₂CH₂CH₂CH₂CH₂— | | O | CH | 1-Pyrazolyl | |
| —CH₂CH₂CH₂CH₂CH₂CH₂— | | O | CH | 1-Pyrazolyl | |
| —CH₂CH₂OCH₂CH₂— | | O | CH | 1-Pyrazolyl | |
| CH₃ | CH₃ | S | CH | 1-Pyrazolyl | |
| CH₃ | CH₃ | O | N | 1-Methyl-pyrazol-3-yl | |
| CH₃ | CH₃ | O | CH | 1-Methyl-pyrazol-3-yl | |
| CH₃ | CH₃ | S | CH | 1-Methyl-pyrazol-3-yl | |
| CH₃ | CH₃ | O | N | 1-Methyl-pyrazol-4-yl | |
| CH₃ | CH₃ | O | CH | 1-Methyl-pyrazol-4-yl | |
| CH₃ | CH₃ | S | CH | 1-Methyl-pyrazol-4-yl | |
| CH₃ | CH₃ | O | N | 1-Methyl-pyrazol-5-yl | |
| CH₃ | CH₃ | O | CH | 1-Methyl-pyrazol-5-yl | |
| CH₃ | CH₃ | S | CH | 1-Methyl-pyrazol-5-yl | |
| CH₃ | CH₃ | O | CH | Benzpyrazol-1-yl | |
| CH₃ | CH₃ | O | CH | 1-Methyl-benzpyrazol-3-yl | |
| CH₃ | CH₃ | O | CH | 3,5-Dimethylpyrazol-1-yl | |
| CH₃ | CH₃ | O | CH | 3(5)-Methyl-pyrazol-1-yl | |
| CH₃ | CH₃ | O | CH | 4-Methylpyrazol-1-yl | |
| CH₃ | CH₃ | O | CH | 4-chloropyrazol-1-yl | |
| CH₃ | CH₃ | O | CH | 4-bromopyrazol-1-yl | |
| CH₃ | CH₃ | O | CH | 4-Phenylpyrazol-1-yl | |
| CH₃ | CH₃ | O | CH | 3,4,5-Trimethylpyrazol-1-yl | |
| CH₃ | CH₃ | O | CH | 4-chloro-3,5-dimethylpyrazol-1-yl | |
| CH₃ | CH₃ | O | CH | 4-Isopropylpyrazol-1-yl | |
| CH₃ | CH₃ | O | CH | 3(5)-Phenylpyrazol-1-yl | |
| CH₃ | CH₃ | O | CH | 3(5)-Methyl-5(3)-phenylpyrazol-1-yl | |
| CH₃ | CH₃ | O | CH | 3,5-Bistrifluoromethylpyrazol-1-yl | |
| CH₃ | CH₃ | O | CH | 4-Nitropyrazol-1-yl | |
| CH₃ | CH₃ | O | CH | 1-Phenylpyrazol-4-yl | |

TABLE 1-continued

Compounds I in which R¹ is a radical ONR⁶R⁷

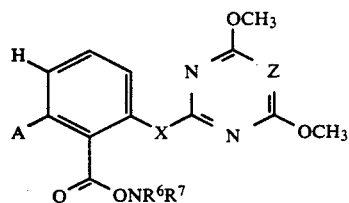

| R⁶ | R⁷ | X | Z | A | Phys. data m.p. [°C.] |
|---|---|---|---|---|---|
| CH₃ | CH₃ | O | CH | 1,3,5-Trimethylpyrazol-4-yl | |
| CH₃ | CH₃ | O | CH | 1-Phenylpyrazol-5-yl | |
| CH₃ | CH₃ | O | CH | 1-Phenylpyrazol-3-yl | |
| CH₃ | CH₃ | O | CH | 1,4-Dimethylpyrazol-3-yl | |
| CH₃ | CH₃ | O | CH | 5-Methyl-1-phenylpyrazol-3-yl | |
| CH₃ | CH₃ | O | CH | 1,5-Dimethylpyrazol-3-yl | |
| CH₃ | CH₃ | O | CH | 1,3-Dimethylpyrazol-4-yl | |
| CH₃ | CH₃ | O | CH | 1,5-Dimethylpyrazol-4-yl | |
| CH₃ | CH₃ | O | CH | -Methyl-1-phenylpyrazol-4-yl | |
| CH₃ | CH₃ | O | CH | 5-Methyl-1-phenylpyrazol-4-yl | |
| CH₃ | CH₃ | O | CH | 3,5-Dimethyl-1-phenylpyrazol-4-yl | |
| CH₃ | CH₃ | O | CH | 3-Methyl-1-phenylpyrazol-5-yl | |
| CH₃ | CH₃ | O | CH | 1,4-Dimethylpyrazol-5-yl | |
| CH₃ | CH₃ | O | CH | 1,3-Dimethylpyrazol-5-yl | |
| CH₃ | CH₃ | O | CH | 1-Imidazolyl | |
| CH₃ | CH₃ | O | CH | 1-Imidazolyl | |
| H | H | O | CH | 1-Imidazolyl | |
| CH₃ | H | O | CH | 1-Imidazolyl | |
| CH₃ | C₂H₅ | O | CH | 1-Imidazolyl | |
| C₂H₅ | C₂H₅ | O | CH | 1-Imidazolyl | |
| H | n-C₃H₇ | O | CH | 1-Imidazolyl | |
| n-C₃H₇ | n-C₃H₇ | O | CH | 1-Imidazolyl | |
| H | i-C₃H₇ | O | CH | 1-Imidazolyl | |
| H | n-C₄H₉ | O | CH | 1-Imidazolyl | |
| H | t-C₄H₉ | O | CH | 1-Imidazolyl | |
| CH₂CH=CH₂ | CH₂CH=CH₂ | O | CH | 1-Imidazolyl | |
| CH₂C≡CH | CH₂C≡CH | O | CH | 1-Imidazolyl | |
| CH₂CH₂Cl | CH₂CH₂Cl | O | CH | 1-Imidazolyl | |
| (CH₂)₂OCH₃ | (CH₂)₂OCH₃ | O | CH | 1-Imidazolyl | |
| CH₂CO₂CH₃ | CH₂CO₂CH₃ | O | CH | 1-Imidazolyl | |
| CH₃ | CH₂CO₂CH₃ | O | CH | 1-Imidazolyl | |
| CH₂CN | CH₂CN | O | CH | 1-Imidazolyl | |
| CH₂CH₂CN | CH₂CH₂CN | O | CH | 1-Imidazolyl | |
| H | Cyclohexyl | O | CH | 1-Imidazolyl | |
| H | CH₂C₆H₅ | O | CH | 1-Imidazolyl | |
| CH₂C₆H₅ | CH₂C₆H₅ | O | CH | 1-Imidazolyl | |
| CH₃ | C₆H₅ | O | CH | 1-Imidazolyl | |
| (CH₂)₂SCH₃ | (CH₂)₂SCH₃ | O | CH | 1-Imidazolyl | |
| —CH₂CH₂CH₂CH₂— | | O | CH | 1-Imidazolyl | |
| —CH₂CH₂CH₂CH₂CH₂— | | O | CH | 1-Imidazolyl | |
| —CH₂CH₂CH₂CH₂CH₂CH₂— | | O | CH | 1-Imidazolyl | |
| —CH₂CH₂OCH₂CH₂— | | O | CH | 1-Imidazolyl | |
| CH₃ | CH₃ | S | CH | 1-Imidazolyl | |
| CH₃ | CH₃ | O | N | 1-Methyl-imidazol-2-yl | |
| CH₃ | CH₃ | O | CH | 1-Methyl-imidazol-2-yl | |
| CH₃ | CH₃ | S | CH | 1-Methyl-imidazol-2-yl | |
| CH₃ | CH₃ | O | N | 1-Methyl-imidazol-4-yl | |
| CH₃ | CH₃ | O | CH | 1-Methyl-imidazol-4-yl | |
| CH₃ | CH₃ | S | CH | 1-Methyl-imidazol-4-yl | |
| CH₃ | CH₃ | O | N | 1-Methyl-imidazol-5-yl | |
| CH₃ | CH₃ | O | CH | 1-Methyl-imidazol-5-yl | |
| CH₃ | CH₃ | S | CH | 1-Methyl-imidazol-5-yl | |
| CH₃ | CH₃ | O | CH | Benzimidazol-1-yl | |
| CH₃ | CH₃ | O | CH | 1-Methyl-benz-imidazol-2-yl | |
| CH₃ | CH₃ | O | CH | 4,5-Dimethylimidazol-1-yl | |
| CH₃ | CH₃ | O | CH | 2-Phenylimidazol-1-yl | |
| CH₃ | CH₃ | O | CH | 4,5-Dichloroimidazol-1-yl | |
| CH₃ | CH₃ | O | CH | 2,4,5-Trichloroimidazol-1-yl | |
| CH₃ | CH₃ | O | CH | 2-Methyl-4,5-dichloroimidazol-1-yl | |
| CH₃ | CH₃ | O | CH | 2-Methyl-4,5-dibromo-imidazol-1-yl | |
| CH₃ | CH₃ | O | CH | 4(5)-chloro-5(4)-methylimidazol-1-yl | |
| CH₃ | CH₃ | O | CH | 4(5)-Nitroimidazol-1-yl | |
| CH₃ | CH₃ | O | CH | 1,4-Dimethyl-imidazol-5-yl | |
| CH₃ | CH₃ | O | CH | 1-Methyl-5-nitro-imidazol-2-yl | |
| CH₃ | CH₃ | O | CH | 1-Phenylimidazol-5-yl | |
| CH₃ | CH₃ | O | N | 1,2,3-Triazol-1-yl | |
| CH₃ | CH₃ | O | CH | 1,2,3-Triazol-1-yl | |

TABLE 1-continued

Compounds I in which $R^1$ is a radical $ONR^6R^7$

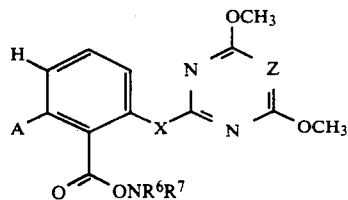

| $R^6$ | $R^7$ | X | Z | A | Phys. data m.p. [°C.] |
|---|---|---|---|---|---|
| CH$_3$ | CH$_3$ | S | CH | 1,2,3-Triazol-1-yl | |
| H | H | O | CH | 1,2,3-Triazol-1-yl | |
| CH$_3$ | H | O | CH | 1,2,3-Triazol-1-yl | |
| CH$_3$ | C$_2$H$_5$ | O | CH | 1,2,3-Triazol-1-yl | |
| C$_2$H$_5$ | C$_2$H$_5$ | O | CH | 1,2,3-Triazol-1-yl | |
| H | n-C$_3$H$_7$ | O | CH | 1,2,3-Triazol-1-yl | |
| n-C$_3$H$_7$ | n-C$_3$H$_7$ | O | CH | 1,2,3-Triazol-1-yl | |
| H | i-C$_3$H$_7$ | O | CH | 1,2,3-Triazol-1-yl | |
| H | n-C$_4$H$_9$ | O | CH | 1,2,3-Triazol-1-yl | |
| H | t-C$_4$H$_9$ | O | CH | 1,2,3-Triazol-1-yl | |
| CH$_2$CH=CH$_2$ | CH$_2$CH=CH$_2$ | O | CH | 1,2,3-Triazol-1-yl | |
| CH$_2$C≡CH | CH$_2$C≡CH | O | CH | 1,2,3-Triazol-1-yl | |
| CH$_2$CH$_2$Cl | CH$_2$CH$_2$Cl | O | CH | 1,2,3-Triazol-1-yl | |
| (CH$_2$)$_2$OCH$_3$ | (CH$_2$)$_2$OCH$_3$ | O | CH | 1,2,3-Triazol-1-yl | |
| CH$_2$CO$_2$CH$_3$ | CH$_2$CO$_2$CH$_3$ | O | CH | 1,2,3-Triazol-1-yl | |
| CH$_3$ | CH$_2$CO$_2$CH$_3$ | O | CH | 1,2,3-Triazol-1-yl | |
| CH$_2$CN | CH$_2$CN | O | CH | 1,2,3-Triazol-1-yl | |
| CH$_2$CH$_2$CN | CH$_2$CH$_2$CN | O | CH | 1,2,3-Triazol-1-yl | |
| H | Cyclohexyl | O | CH | 1,2,3-Triazol-1-yl | |
| H | CH$_2$C$_6$H$_5$ | O | CH | 1,2,3-Triazol-1-yl | |
| CH$_2$C$_6$H$_5$ | CH$_2$C$_6$H$_5$ | O | CH | 1,2,3-Triazol-1-yl | |
| CH$_3$ | C$_6$H$_5$ | O | CH | 1,2,3-Triazol-1-yl | |
| (CH$_2$)$_2$SCH$_3$ | (CH$_2$)$_2$SCH$_3$ | O | CH | 1,2,3-Triazol-1-yl | |
| —CH$_2$CH$_2$CH$_2$CH$_2$— | | O | CH | 1,2,3-Triazol-1-yl | |
| —CH$_2$CH$_2$CH$_2$CH$_2$CH$_2$— | | O | CH | 1,2,3-Triazol-1-yl | |
| —CH$_2$CH$_2$CH$_2$CH$_2$CH$_2$CH$_2$— | | O | CH | 1,2,3-Triazol-1-yl | |
| —CH$_2$CH$_2$OCH$_2$CH$_2$— | | O | CH | 1,2,3-Triazol-1-yl | |
| CH$_3$ | CH$_3$ | O | CH | 1-Methyl-1,2,3triazol-4-yl | |
| CH$_3$ | CH$_3$ | O | CH | 1-Methyl-1,2,3triazol-4-yl | |
| CH$_3$ | CH$_3$ | S | CH | 1-Methyl-1,2,3triazol-4-yl | |
| CH$_3$ | CH$_3$ | O | N | 1-Methyl-1,2,3triazol-5-yl | |
| CH$_3$ | CH$_3$ | O | CH | 1-Methyl-1,2,3triazol-5-yl | |
| CH$_3$ | CH$_3$ | S | CH | 1-Methyl-1,2,3triazol-5-yl | |
| CH$_3$ | CH$_3$ | O | CH | Benz-1,2,3-triazol-1-yl | |
| CH$_3$ | CH$_3$ | O | CH | 4,5-Dimethyl-1,2,3-triazol-1-yl | |
| CH$_3$ | CH$_3$ | O | CH | 4(5)-Phenyl-1,2,3-triazol-1-yl | |
| CH$_3$ | CH$_3$ | O | CH | 1-Phenyl-1,2,3-triazol-4-yl | |
| CH$_3$ | CH$_3$ | O | CH | 1-Phenyl-1,2,3-triazol-4-yl | |
| CH$_3$ | CH$_3$ | O | CH | 5-methyl-1-phenyl-1,2,3-triazol-4-yl | |
| CH$_3$ | CH$_3$ | O | N | 1,2,4-Triazol-1-yl | |
| CH$_3$ | CH$_3$ | O | CH | 1,2,4-Triazol-1-yl | |
| CH$_3$ | CH$_3$ | S | CH | 1,2,4-Triazol-1-yl | |
| H | H | O | CH | 1,2,4-Triazol-1-yl | |
| CH$_3$ | H | O | CH | 1,2,4-Triazol-1-yl | |
| CH$_3$ | C$_2$H$_5$ | O | CH | 1,2,4-Triazol-1-yl | |
| C$_2$H$_5$ | C$_2$H$_5$ | O | CH | 1,2,4-Triazol-1-yl | |
| H | n-C$_3$H$_7$ | O | CH | 1,2,4-Triazol-1-yl | |
| n-C$_3$H$_7$ | n-C$_3$H$_7$ | O | CH | 1,2,4-Triazol-1-yl | |
| H | i-C$_3$H$_7$ | O | CH | 1,2,4-Triazol-1-yl | |
| H | n-C$_4$H$_9$ | O | CH | 1,2,4-Triazol-1-yl | |
| H | t-C$_4$H$_9$ | O | CH | 1,2,4-Triazol-1-yl | |
| CH$_2$CH=CH$_2$ | CH$_2$CH=CH$_2$ | O | CH | 1,2,4-Triazol-1-yl | |
| CH$_2$C≡CH | CH$_2$C≡CH | O | CH | 1,2,4-Triazol-1-yl | |
| CH$_2$CH$_2$Cl | CH$_2$CH$_2$Cl | O | CH | 1,2,4-Triazol-1-yl | |
| (CH$_2$)$_2$OCH$_3$ | (CH$_2$)$_2$OCH$_3$ | O | CH | 1,2,4-Triazol-1-yl | |
| CH$_2$CO$_2$CH$_3$ | | O | CH | 1,2,4-Triazol-1-yl | |
| CH$_3$ | CH$_2$CO$_2$CH$_3$ | O | CH | 1,2,4-Triazol-1-yl | |
| CH$_2$CN | CH$_2$CN | O | CH | 1,2,4-Triazol-1-yl | |
| CH$_2$CH$_2$CN | CH$_2$CH$_2$CN | O | CH | 1,2,4-Triazol-1-yl | |
| H | Cyclohexyl | O | CH | 1,2,4-Triazol-1-yl | |
| H | CH$_2$C$_6$H$_5$ | O | CH | 1,2,4-Triazol-1-yl | |
| CH$_2$C$_6$H$_5$ | CH$_2$C$_6$H$_5$ | O | CH | 1,2,4-Triazol-1-yl | |
| CH$_3$ | C$_6$H$_5$ | O | CH | 1,2,4-Triazol-1-yl | |
| (CH$_2$)$_2$SCH$_3$ | (CH$_2$)$_2$SCH$_3$ | O | CH | 1,2,4-Triazol-1-yl | |
| —CH$_2$CH$_2$CH$_2$CH$_2$— | | O | CH | 1,2,4-Triazol-1-yl | |
| —CH$_2$CH$_2$CH$_2$CH$_2$CH$_2$— | | O | CH | 1,2,4-Triazol-1-yl | |
| —CH$_2$CH$_2$CH$_2$CH$_2$CH$_2$CH$_2$— | | O | CH | 1,2,4-Triazol-1-yl | |

TABLE 1-continued

Compounds I in which R¹ is a radical ONR⁶R⁷

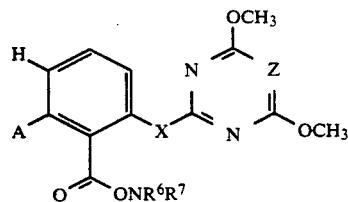

| R⁶ | R⁷ | X | Z | A | Phys. data m.p. [°C.] |
|---|---|---|---|---|---|
| —CH₂CH₂OCH₂CH₂— | | O | CH | 1,2,4-Triazol-1-yl | |
| CH₃ | CH₃ | O | N | 1-Methyl-1,2,4-triazol-3-yl | |
| CH₃ | CH₃ | O | CH | 1-Methyl-1,2,4-triazol-3-yl | |
| CH₃ | CH₃ | S | CH | 1-Methyl-1,2,4-triazol-3-yl | |
| CH₃ | CH₃ | O | N | 1-Methyl-1,2,4-triazol-5-yl | |
| CH₃ | CH₃ | O | CH | 1-Methyl-1,2,4-triazol-5-yl | |
| CH₃ | CH₃ | S | CH | 1-Methyl-1,2,4-triazol-5-yl | |
| CH₃ | CH₃ | O | CH | 3(5)-Phenyl-1,2,4-triazol-1-yl | |
| CH₃ | CH₃ | O | CH | 3,5-Dimethyl-1,2,4-triazol-1-yl | |
| CH₃ | CH₃ | O | CH | 5-Methyl-1-phenyl-1,2,4-triazol-3-yl | |
| CH₃ | CH₃ | O | N | 1-Tetrazolyl | |
| CH₃ | CH₃ | O | CH | 1-Tetrazolyl | |
| CH₃ | CH₃ | O | CH | 1-Tetrazolyl | |
| CH₃ | CH₃ | O | CH | 1-Methyl-tetrazol-5-yl | |
| CH₃ | CH₃ | O | CH | 1-Methyl-tetrazol-5-yl | |
| CH₃ | CH₃ | S | CH | 1-Methyl-tetrazol-5-yl | |
| CH₃ | CH₃ | O | N | 2-Oxazolyl | |
| CH₃ | CH₃ | O | CH | 2-Oxazolyl | |
| CH₃ | CH₃ | S | CH | 2-Oxazolyl | |
| CH₃ | CH₃ | O | N | 4-Oxazolyl | |
| CH₃ | CH₃ | O | CH | 4-Oxazolyl | |
| CH₃ | CH₃ | S | CH | 4-Oxazolyl | |
| CH₃ | CH₃ | O | N | 5-Oxazolyl | |
| CH₃ | CH₃ | O | CH | 5-Oxazolyl | |
| CH₃ | CH₃ | S | CH | 5-Oxazolyl | |
| CH₃ | CH₃ | O | CH | 2-Methyloxazol-4-yl | |
| CH₃ | CH₃ | O | CH | Benzoxazol-2-yl | |
| CH₃ | CH₃ | O | N | Isoxazol-3-yl | |
| CH₃ | CH₃ | O | CH | Isoxazol-3-yl | |
| CH₃ | CH₃ | S | CH | Isoxazol-3-yl | |
| CH₃ | CH₃ | O | N | Isoxazol-4-yl | |
| CH₃ | CH₃ | O | CH | Isoxazol-4-yl | |
| CH₃ | CH₃ | S | CH | Isoxazol-4-yl | |
| CH₃ | CH₃ | O | N | Isoxazol-5-yl | |
| CH₃ | CH₃ | O | CH | Isoxazol-5-yl | |
| CH₃ | CH₃ | S | CH | Isoxazol-5-yl | |
| CH₃ | CH₃ | O | CH | Benzisoxazol-3-yl | |
| CH₃ | CH₃ | O | CH | 3-Methylisoxazol-5-yl | |
| CH₃ | CH₃ | O | CH | 3-Isopropylisoxazol-5-yl | |
| CH₃ | CH₃ | O | CH | 3-Phenylisoxazol-5-yl | |
| CH₃ | CH₃ | O | CH | 3-Methyl-4-chloro-isoxazol-5-yl | |
| CH₃ | CH₃ | O | CH | 3-Methylisoxazol-4-yl | |
| CH₃ | CH₃ | O | CH | 3,5-Dimethyl-isoxazol-4-yl | |
| CH₃ | CH₃ | O | N | 2-Thiazolayl | |
| CH₃ | CH₃ | O | CH | 2-Thiazolyl | |
| CH₃ | CH₃ | S | CH | 2-Thiazolyl | |
| H | H | O | CH | 2-Thiazolyl | |
| CH₃ | H | O | CH | 2-Thiazolyl | |
| CH₃ | C₂H₅ | O | CH | 2-Thiazolyl | |
| C₂H₅ | C₂H₅ | O | CH | 2-Thiazolyl | |
| H | n-C₃H₇ | O | CH | 2-Thiazolyl | |
| n-C₃H₇ | n-C₃H₇ | O | CH | 2-Thiazolyl | |
| H | i-C₃H₇ | O | CH | 2-Thiazolyl | |
| H | n-C₄H₉ | O | CH | 2-Thiazolyl | |
| H | t-C₄H₉ | O | CH | 2-Thiazolyl | |
| CH₂CH=CH₂ | CH₂CH=CH₂ | O | CH | 2-Thiazolyl | |
| CH₂C≡CH | CH₂C≡CH | O | CH | 2-Thiazolyl | |
| CH₂CH₂Cl | CH₂CH₂Cl | O | CH | 2-Thiazolyl | |
| (CH₂)₂OCH₃ | (CH₂)₂OCH₃ | O | CH | 2-Thiazolyl | |
| CH₂CO₂CH₃ | CH₂CO₂CH₃ | O | CH | 2-Thiazolyl | |
| CH₃ | CH₂CO₂CH₃ | O | CH | 2-Thiazolyl | |
| CH₂CN | CH₂CN | O | CH | 2-Thiazolyl | |
| CH₂CH₂CN | CH₂CH₂CN | O | CH | 2-Thiazolyl | |
| H | Cyclohexyl | O | CH | 2-Thiazolyl | |
| H | CH₂C₆H₅ | O | CH | 2-Thiazolyl | |
| CH₂C₆H₅ | CH₂C₆H₅ | O | CH | 2-Thiazolyl | |
| CH₃ | C₆H₅ | O | CH | 2-Thiazolyl | |

TABLE 1-continued

Compounds I in which $R^1$ is a radical $ONR^6R^7$

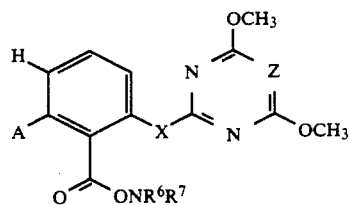

| $R^6$ | $R^7$ | X | Z | A | Phys. data m.p. [°C.] |
|---|---|---|---|---|---|
| (CH$_2$)$_2$SCH$_3$ | (CH$_2$)$_2$SCH$_3$ | O | CH | 2-Thiazolyl | |
| —CH$_2$CH$_2$CH$_2$CH$_2$— | | O | CH | 2-Thiazolyl | |
| —CH$_2$CH$_2$CH$_2$CH$_2$CH$_2$— | | O | CH | 2-Thiazolyl | |
| —CH$_2$CH$_2$CH$_2$CH$_2$CH$_2$CH$_2$— | | O | CH | 2-Thiazolyl | |
| —CH$_2$CH$_2$OCH$_2$CH$_2$— | | O | CH | 2-Thiazolyl | |
| CH$_3$ | CH$_3$ | O | N | 4-Thiazolyl | |
| CH$_3$ | CH$_3$ | O | CH | 4-Thiazolyl | |
| CH$_3$ | CH$_3$ | S | CH | 4-Thiazolyl | |
| CH$_3$ | CH$_3$ | O | N | 5-Thiazolyl | |
| CH$_3$ | CH$_3$ | O | CH | 5-Thiazolyl | |
| CH$_3$ | CH$_3$ | S | CH | 5-Thiazolyl | |
| CH$_3$ | CH$_3$ | O | CH | Benzthiazol-2-yl | |
| CH$_3$ | CH$_3$ | O | CH | 2-Methylthiazol-4-yl | |
| CH$_3$ | CH$_3$ | O | CH | 2-Phenylthiazol-4-yl | |
| CH$_3$ | CH$_3$ | O | CH | 2-Benzylthiazol-4-yl | |
| CH$_3$ | CH$_3$ | O | CH | 5-chloro-2-phenylthiazol-4-yl | |
| CH$_3$ | CH$_3$ | O | CH | 4-Methylthiazol-2-yl | |
| CH$_3$ | CH$_3$ | O | CH | 5-Methylthiazol-2-yl | |
| CH$_3$ | CH$_3$ | O | CH | 4-Phenylthiazol-2-yl | |
| CH$_3$ | CH$_3$ | O | CH | 4-Methylthiazol-5-yl | |
| CH$_3$ | CH$_3$ | O | CH | 2-Methylthiazol-5-yl | |
| CH$_3$ | CH$_3$ | O | CH | 2-Phenylthiazol-5-yl | |
| CH$_3$ | CH$_3$ | O | N | Isothiazol-3-yl | |
| CH$_3$ | CH$_3$ | O | CH | Isothiazol-3-yl | |
| CH$_3$ | CH$_3$ | S | CH | Isothiazol-3-yl | |
| CH$_3$ | CH$_3$ | O | N | Isothiazol-4-yl | |
| CH$_3$ | CH$_3$ | O | CH | Isothiazol-4-yl | |
| CH$_3$ | CH$_3$ | S | CH | Isothiazol-4-yl | |
| CH$_3$ | CH$_3$ | O | N | Isothiazol-5-yl | |
| CH$_3$ | CH$_3$ | O | CH | Isothiazol-5-yl | |
| CH$_3$ | CH$_3$ | S | CH | Isothiazol-5-yl | |
| CH$_3$ | CH$_3$ | O | CH | Benzisothiazol-3-yl | |
| CH$_3$ | CH$_3$ | O | N | 1,2,3-Thiadiazol-4-yl | |
| CH$_3$ | CH$_3$ | O | CH | 1,2,3-Thiadiazol-4-yl | |
| CH$_3$ | CH$_3$ | S | CH | 1,2,3-Thiadiazol-4-yl | |
| CH$_3$ | CH$_3$ | O | N | 1,2,3-Thiadiazol-5-yl | |
| CH$_3$ | CH$_3$ | O | CH | 1,2,3-Thiadiazol-5-yl | |
| CH$_3$ | CH$_3$ | S | CH | 1,2,3-Thiadiazol-5-yl | |
| CH$_3$ | CH$_3$ | O | N | 1,3,4-Thiadiazol-2-yl | |
| CH$_3$ | CH$_3$ | O | CH | 1,3,4-Thiadiazol-2-yl | |
| CH$_3$ | CH$_3$ | S | CH | 1,3,4-Thiadiazol-2-yl | |
| CH$_3$ | CH$_3$ | O | N | 1,3,4-Thiadiazol-5-yl | |
| CH$_3$ | CH$_3$ | O | CH | 1,3,4-Thiadiazol-5-yl | |
| CH$_3$ | CH$_3$ | S | CH | 1,3,4-Thiadiazol-5-yl | |
| CH$_3$ | CH$_3$ | O | CH | 5-Methyl-1,3,4-thiadiazol-2-yl | |
| CH$_3$ | CH$_3$ | O | CH | 5-Phenyl-1,3,4-thiadiazol-2-yl | |
| CH$_3$ | CH$_3$ | O | N | 1,2,3-Oxadiazol-4-yl | |
| CH$_3$ | CH$_3$ | O | CH | 1,2,3-Oxadiazol-4-yl | |
| CH$_3$ | CH$_3$ | S | CH | 1,2,3-Oxadiazol-4-yl | |
| CH$_3$ | CH$_3$ | O | N | 1,2,3-Oxadiazol-5-yl | |
| CH$_3$ | CH$_3$ | O | CH | 1,2,3-Oxadiazol-5-yl | |
| CH$_3$ | CH$_3$ | O | N | 1,2,4-Oxadiazol-3-yl | |
| CH$_3$ | CH$_3$ | O | CH | 1,2,4-Oxadiazol-3-yl | |
| CH$_3$ | CH$_3$ | S | CH | 1,2,4-Oxadiazol-3-yl | |
| CH$_3$ | CH$_3$ | O | N | 1,2,4-Oxadiazol-5-yl | |
| CH$_3$ | CH$_3$ | O | CH | 1,2,4-Oxadiazol-5-yl | |
| CH$_3$ | CH$_3$ | S | CH | 1,2,4-Oxadiazol-5-yl | |
| CH$_3$ | CH$_3$ | O | N | 1,2,3,4-Thiatriazol-5-yl | |
| CH$_3$ | CH$_3$ | O | CH | 1,2,3,4-Thiatriazol-5-yl | |
| CH$_3$ | CH$_3$ | S | CH | 1,2,3,4-Thiatriazol-5-yl | |
| CH$_3$ | CH$_3$ | O | N | 2-Pyridyl | |
| CH$_3$ | CH$_3$ | O | CH | 2-Pyridyl | |
| CH$_3$ | CH$_3$ | S | CH | 2-Pyridyl | |
| H | H | O | CH | 2-Pyridyl | |
| CH$_3$ | H | O | CH | 2-Pyridyl | |
| CH$_3$ | C$_2$H$_5$ | O | CH | 2-Pyridyl | |
| C$_2$H$_5$ | C$_2$H$_5$ | O | CH | 2-Pyridyl | |

TABLE 1-continued

Compounds I in which $R^1$ is a radical $ONR^6R^7$

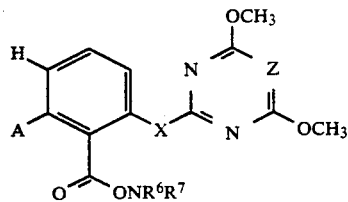

| $R^6$ | $R^7$ | X | Z | A | Phys. data m.p. [°C.] |
|---|---|---|---|---|---|
| H | n-$C_3H_7$ | O | CH | 2-Pyridyl | |
| n-$C_3H_7$ | n-$C_3H_7$ | O | CH | 2-Pyridyl | |
| H | i-$C_3H_7$ | O | CH | 2-Pyridyl | |
| H | n-$C_4H_9$ | O | CH | 2-Pyridyl | |
| H | t-$C_4H_9$ | O | CH | 2-Pyridyl | |
| $CH_2CH=CH_2$ | $CH_2CH=CH_2$ | O | CH | 2-Pyridyl | |
| $CH_2C≡CH$ | $CH_2C≡CH$ | O | CH | 2-Pyridyl | |
| $CH_2CH_2Cl$ | $CH_2CH_2Cl$ | O | CH | 2-Pyridyl | |
| $(CH_2)_2OCH_3$ | $(CH_2)_2OCH_3$ | O | CH | 2-Pyridyl | |
| $CH_2CO_2CH_3$ | $CH_2CO_2CH_3$ | O | CH | 2-Pyridyl | |
| $CH_3$ | $CH_2CO_2CH_3$ | O | CH | 2-Pyridyl | |
| $CH_2CN$ | $CH_2CN$ | O | CH | 2-Pyridyl | |
| $CH_2CH_2CN$ | $CH_2CH_2CN$ | O | CH | 2-Pyridyl | |
| H | Cyclohexyl | O | CH | 2-Pyridyl | |
| H | $CH_2C_6H_5$ | O | CH | 2-Pyridyl | |
| $CH_2C_6H_5$ | $CH_2C_6H_5$ | O | CH | 2-Pyridyl | |
| $CH_3$ | $C_6H_5$ | O | CH | 2-Pyridyl | |
| $(CH_2)_2SCH_3$ | $(CH_2)_2SCH_3$ | O | CH | 2-Pyridyl | |
| —$CH_2CH_2CH_2CH_2$— | | O | CH | 2-Pyridyl | |
| —$CH_2CH_2CH_2CH_2CH_2$— | | O | CH | 2-Pyridyl | |
| —$CH_2CH_2CH_2CH_2CH_2CH_2$— | | O | CH | 2-Pyridyl | |
| —$CH_2CH_2OCH_2CH_2$— | | O | CH | 2-Pyridyl | |
| $CH_3$ | $CH_3$ | O | N | 3-Pyridyl | |
| $CH_3$ | $CH_3$ | O | CH | 3-Pyridyl | |
| $CH_3$ | $CH_3$ | S | CH | 3-Pyridyl | |
| H | H | O | CH | 3-Pyridyl | |
| $CH_3$ | H | O | CH | 3-Pyridyl | |
| $CH_3$ | $C_2H_5$ | O | CH | 3-Pyridyl | |
| $C_2H_5$ | $C_2H_5$ | O | CH | 3-Pyridyl | |
| n-$C_3H_7$ | $OCH_3$ | O | CH | 3-Pyridyl | |
| n-$C_3H_7$ | n-$C_3H_7$ | O | CH | 3-Pyridyl | |
| H | i-$C_3H_7$ | O | CH | 3-Pyridyl | |
| H | n-$C_4H_9$ | O | CH | 3-Pyridyl | |
| H | t-$C_4H_9$ | O | CH | 3-Pyridyl | |
| $CH_2CH=CH_2$ | $CH_2CH=CH_2$ | O | CH | 3-Pyridyl | |
| $CH_2C≡CH$ | $CH_2C≡CH$ | O | CH | 3-Pyridyl | |
| $CH_2CH_2Cl$ | $CH_2CH_2Cl$ | O | CH | 3-Pyridyl | |
| $(CH_2)_2OCH_3$ | $(CH_2)_2OCH_3$ | O | CH | 3-Pyridyl | |
| $CH_2CO_2CH_3$ | $CH_2CO_2CH_3$ | O | CH | 3-Pyridyl | |
| $CH_3$ | $CH_2CO_2CH_3$ | O | CH | 3-Pyridyl | |
| $CH_2CN$ | $CH_2CN$ | O | CH | 3-Pyridyl | |
| $CH_2CH_2CN$ | $CH_2CH_2CN$ | O | CH | 3-Pyridyl | |
| H | Cyclohexyl | O | CH | 3-Pyridyl | |
| H | $CH_2C_6H_5$ | O | CH | 3-Pyridyl | |
| $CH_2C_6H_5$ | $CH_2C_6H_5$ | O | CH | 3-Pyridyl | |
| $CH_3$ | $C_6H_5$ | O | CH | 3-Pyridyl | |
| $(CH_2)_2SCH_3$ | $(CH_2)_2SCH_3$ | O | CH | 3-Pyridyl | |
| —$CH_2CH_2CH_2CH_2$— | | O | CH | 3-Pyridyl | |
| —$CH_2CH_2CH_2CH_2CH_2$— | | O | CH | 3-Pyridyl | |
| —$CH_2CH_2CH_2CH_2CH_2CH_2$— | | O | CH | 3-Pyridyl | |
| —$CH_2CH_2OCH_2CH_2$— | | O | CH | 3-Pyridyl | |
| $CH_3$ | $CH_3$ | O | N | 4-Pyridyl | |
| $CH_3$ | $CH_3$ | O | CH | 4-Pyridyl | |
| $CH_3$ | $CH_3$ | S | CH | 4-Pyridyl | |
| H | H | O | CH | 4-Pyridyl | |
| $CH_3$ | H | O | CH | 4-Pyridyl | |
| $CH_3$ | $C_2H_5$ | O | CH | 4-Pyridyl | |
| $C_2H_5$ | $C_2H_5$ | O | CH | 4-Pyridyl | |
| H | n-$C_3H_7$ | O | CH | 4-Pyridyl | |
| n-$C_3H_7$ | n-$C_3H_7$ | O | CH | 4-Pyridyl | |
| H | i-$C_3H_7$ | O | CH | 4-Pyridyl | |
| H | n-$C_4H_9$ | O | CH | 4-Pyridyl | |
| H | t-$C_4H_9$ | O | CH | 4-Pyridyl | |
| $CH_2CH=CH_2$ | $CH_2CH=CH_2$ | O | CH | 4-Pyridyl | |
| $CH_2C≡CH$ | $CH_2C≡CH$ | O | CH | 4-Pyridyl | |
| $CH_2CH_2Cl$ | $CH_2CH_2Cl$ | O | CH | 4-Pyridyl | |
| $(CH_2)_2OCH_3$ | $(CH_2)_2OCH_3$ | O | CH | 4-Pyridyl | |

TABLE 1-continued

Compounds I in which $R^1$ is a radical $ONR^6R^7$

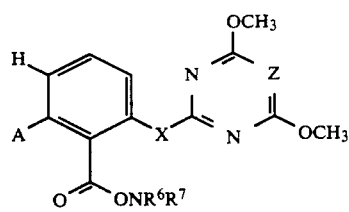

| $R^6$ | $R^7$ | X | Z | A | Phys. data m.p. [°C.] |
|---|---|---|---|---|---|
| CH$_2$CO$_2$CH$_3$ | CH$_2$CO$_2$CH$_3$H | O | CH | 4-Pyridyl | |
| CH$_3$ | CH$_2$CO$_2$CH$_3$ | O | CH | 4-Pyridyl | |
| CH$_2$CN | CH$_2$CN | O | CH | 4-Pyridyl | |
| CH$_2$CH$_2$CN | CH$_2$CH$_2$CN | O | CH | 4-Pyridyl | |
| H | Cyclohexyl | O | CH | 4-Pyridyl | |
| H | CH$_2$C$_6$H$_5$ | O | CH | 4-Pyridyl | |
| CH$_2$C$_6$H$_5$ | CH$_2$C$_6$H$_5$ | O | CH | 4-Pyridyl | |
| CH$_3$ | C$_6$H$_5$ | O | CH | 4-Pyridyl | |
| (CH$_2$)$_2$SCH$_3$ | (CH$_2$)$_2$SCH$_3$ | O | CH | 4-Pyridyl | |
| —CH$_2$CH$_2$CH$_2$CH$_2$— | | O | CH | 4-Pyridyl | |
| —CH$_2$CH$_2$CH$_2$CH$_2$CH$_2$— | | O | CH | 4-Pyridyl | |
| —CH$_2$CH$_2$CH$_2$CH$_2$CH$_2$CH$_2$— | | O | CH | 4-Pyridyl | |
| —CH$_2$CH$_2$OCH$_2$CH$_2$— | | O | CH | 4-Pyridyl | |
| CH$_3$ | CH$_3$ | O | CH | 6-Methyl-2-pyridyl | |
| CH$_3$ | CH$_3$ | O | CH | 3-chloro-5-pyridyl | |
| CH$_3$ | CH$_3$ | O | CH | 5-chloro-2-pyridyl | |
| CH$_3$ | CH$_3$ | O | N | 2-Naphthyl | |
| CH$_3$ | CH$_3$ | O | CH | 2-Naphthyl | |
| CH$_3$ | CH$_3$ | S | CH | 2-Naphthyl | |
| H | H | O | CH | 2-Naphthyl | |
| CH$_3$ | H | O | CH | 2-Naphthyl | |
| CH$_3$ | C$_2$H$_5$ | O | CH | 2-Naphthyl | |
| C$_2$H$_5$ | C$_2$H$_5$ | O | CH | 2-Naphthyl | |
| H | n-C$_3$H$_7$ | O | CH | 2-Naphthyl | |
| n-C$_3$H$_7$ | n-C$_3$H$_7$ | O | CH | 2-Naphthyl | |
| H | i-C$_3$H$_7$ | O | CH | 2-Naphthyl | |
| H | n-C$_4$H$_9$ | O | CH | 2-Naphthyl | |
| H | t-C$_4$H$_9$ | O | CH | 2-Naphthyl | |
| CH$_2$CH=CH$_2$ | CH$_2$CH=CH$_2$ | O | CH | 2-Naphthyl | |
| CH$_2$C≡CH | CH$_2$C≡CH | O | CH | 2-Naphthyl | |
| CH$_2$CH$_2$Cl | CH$_2$CH$_2$Cl | O | CH | 2-Naphthyl | |
| (CH$_2$)$_2$OCH$_3$ | (CH$_2$)$_2$OCH$_3$ | O | CH | 2-Naphthyl | |
| CH$_2$CO$_2$CH$_3$ | CH$_2$CO$_2$CH$_3$ | O | CH | 2-Naphthyl | |
| CH$_3$ | CH$_2$CO$_2$CH$_3$ | O | CH | 2-Naphthyl | |
| CH$_2$CN | CH$_2$CN | O | CH | 2-Naphthyl | |
| CH$_2$CH$_2$CN | CH$_2$CH$_2$CN | O | CH | 2-Naphthyl | |
| H | Cyclohexyl | O | CH | 2-Naphthyl | |
| H | CH$_2$C$_6$H$_5$ | O | CH | 2-Naphthyl | |
| CH$_2$C$_6$H$_5$ | CH$_2$C$_6$H$_5$ | O | CH | 2-Naphthyl | |
| CH$_3$ | C$_6$H$_5$ | O | CH | 2-Naphthyl | |
| (CH$_2$)$_2$SCH$_3$ | (CH$_2$)$_2$SCH$_3$ | O | CH | 2-Naphthyl | |
| —CH$_2$CH$_2$CH$_2$CH$_2$— | | O | CH | 2-Naphthyl | |
| —CH$_2$CH$_2$CH$_2$CH$_2$CH$_2$— | | O | CH | 2-Naphthyl | |
| —CH$_2$CH$_2$CH$_2$CH$_2$CH$_2$CH$_2$— | | O | CH | 2-Naphthyl | |
| —CH$_2$CH$_2$OCH$_2$CH$_2$— | | O | CH | 2-Naphthyl | |
| CH$_3$ | CH$_3$ | O | N | 1-Naphthyl | |
| CH$_3$ | CH$_3$ | O | CH | 1-Naphthyl | |
| CH$_3$ | CH$_3$ | S | CH | 1-Naphthyl | |
| H | H | O | CH | 1-Naphthyl | |
| CH$_3$ | H | O | CH | 1-Naphthyl | |
| CH$_3$ | C$_2$H$_5$ | O | CH | 1-Naphthyl | |
| C$_2$H$_5$ | C$_2$H$_5$ | O | CH | 1-Naphthyl | |
| H | n-C$_3$H$_7$ | O | CH | 1-Naphthyl | |
| n-C$_3$H$_7$ | n-C$_3$H$_7$ | O | CH | 1-Naphthyl | |
| H | i-C$_3$H$_7$ | O | CH | 1-Naphthyl | |
| H | n-C$_4$H$_9$ | O | CH | 1-Naphthyl | |
| H | t-C$_4$H$_9$ | O | CH | 1-Naphthyl | |
| CH$_2$CH=CH$_2$ | CH$_2$CH=CH$_2$ | O | CH | 1-Naphthyl | |
| CH$_2$C≡CH | CH$_2$C≡CH | O | CH | 1-Naphthyl | |
| CH$_2$CH$_2$Cl | CH$_2$CH$_2$Cl | O | CH | 1-Naphthyl | |
| (CH$_2$)$_2$OCH$_3$ | (CH$_2$)$_2$OCH$_3$ | O | CH | 1-Naphthyl | |
| CH$_2$CO$_2$CH$_3$ | CH$_2$CO$_2$CH$_3$ | O | CH | 1-Naphthyl | |
| CH$_3$ | CH$_2$CO$_2$CH$_3$ | O | CH | 1-Naphthyl | |
| CH$_2$CN | CH$_2$CN | O | CH | 1-Naphthyl | |
| CH$_2$CH$_2$CN | CH$_2$CH$_2$CN | O | CH | 1-Naphthyl | |
| H | Cyclohexyl | O | CH | 1-Naphthyl | |
| H | CH$_2$C$_6$H$_5$ | O | CH | 1-Naphthyl | |

TABLE 1-continued

Compounds I in which R¹ is a radical ONR⁶R⁷

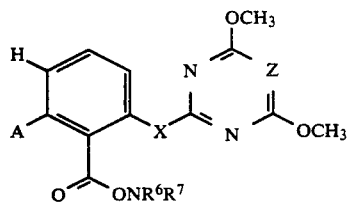

| R⁶ | R⁷ | X | Z | A | Phys. data m.p. [°C.] |
|---|---|---|---|---|---|
| CH₂C₆H₅ | CH₂C₆H₅ | O | CH | 1-Naphthyl | |
| CH₃ | C₆H₅ | O | CH | 1-Naphthyl | |
| (CH₂)₂SCH₃ | (CH₂)₂SCH₃ | O | CH | 1-Naphthyl | |
| —CH₂CH₂CH₂CH₂— | | O | CH | 1-Naphthyl | |
| —CH₂CH₂CH₂CH₂CH₂— | | O | CH | 1-Naphthyl | |
| —CH₂CH₂CH₂CH₂CH₂CH₂— | | O | CH | 1-Naphthyl | |
| —CH₂CH₂OCH₂CH₂— | | O | CH | 1-Naphthyl | |
| CH₃ | CH₃ | O | CH | 2-Methyl-1-naphthyl | |
| CH₃ | CH₃ | O | CH | 2-Methoxy-1-naphthyl | |
| CH₃ | CH₃ | O | CH | 1-chloro-4-naphthyl | |
| CH₃ | CH₃ | O | N | 2-quinolinyl | |
| CH₃ | CH₃ | O | CH | 2-quinolinyl | |
| CH₃ | CH₃ | S | CH | 2-quinolinyl | |
| CH₃ | CH₃ | O | N | 4-quinolinyl | |
| CH₃ | CH₃ | O | CH | 4-quinolinyl | |
| CH₃ | CH₃ | S | CH | 4-quinolinyl | |
| CH₃ | CH₃ | O | CH | 2-chloro-quinolin-2-yl | |
| CH₃ | CH₃ | O | CH | 2,6-Dichloro-quinolin-3-yl | |
| CH₃ | CH₃ | O | CH | 2-chloro-6-methyl-quinolin-3-yl | |

TABLE 2

Compounds I in which R¹ is a radical OR⁵ (R, R³ = OCH₃, R⁴ = H).

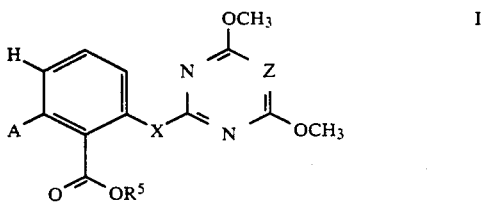

| R⁵ | X | Z | A | Phys. data m.p. [°C.] |
|---|---|---|---|---|
| 1-Pyrazolyl | O | N | 1-Pyrrolyl | |
| 1-Pyrazolyl | O | CH | 1-Pyrrolyl | |
| 1-Pyrazolyl | S | CH | 1-Pyrrolyl | |
| 1-Pyrazolyl | O | N | 1-Methyl-pyrrol-2-yl | |
| 1-Pyrazolyl | O | CH | 1-Methyl-pyrrol-2-yl | |
| 1-Pyrazolyl | S | CH | 1-Methyl-pyrrol-2-yl | |
| 1-Pyrazolyl | O | N | 1-Methyl-pyrrol-3-yl | |
| 1-Pyrazolyl | O | CH | 1-Methyl-pyrrol-3-yl | |
| 1-Pyrazolyl | S | CH | 1-Methyl-pyrrol-3-yl | |
| 1-Pyrazolyl | O | CH | 1-Indolyl | |
| 1-Pyrazolyl | O | CH | 1-Methyl-indol-2-yl | |
| 1-Pyrazolyl | O | CH | 1-Methyl-indol-3-yl | |
| 1-Pyrazolyl | O | CH | 3-Methyl-indol-1-yl | |
| 1-Pyrazolyl | O | CH | 3,5-Dimethyl-pyrrol-1-yl | |
| 1-Pyrazolyl | O | CH | 3-Methylpyrrol-1-yl | |
| 1-Pyrazolyl | O | CH | 4-Methylpyrrol-1-yl | |
| 1-Pyrazolyl | O | CH | 4-chloropyrrol-1-yl | |
| 1-Pyrazolyl | O | CH | 4-bromopyrrol-1-yl | |
| 1-Pyrazolyl | O | CH | 4-Phenylpyrrol-1-yl | |
| 1-Pyrazolyl | O | CH | 3,4,5-Trimethyl-pyrrol-1-yl | |
| 1-Pyrazolyl | O | CH | 4-chloro-3,5-dimethyl-pyrrol-1-yl | |
| 1-Pyrazolyl | O | CH | 4-Isopropylpyrrol-1-yl | |
| 1-Pyrazolyl | O | CH | 3-Phenylpyrrol-1-yl | |
| 1-Pyrazolyl | O | CH | 3-Methyl-5-phenyl-pyrrol-1-yl | |
| 1-Pyrazolyl | O | CH | 3,5-Bistrifluoromethyl-pyrrol-1-yl | |
| 1-Pyrazolyl | O | CH | 4-Nitropyrrol-1-yl | |
| 1-Pyrazolyl | O | CH | 1-Phenylpyrrol-3-yl | |
| 1-Pyrazolyl | O | CH | 1,3,5-Trimethyl-pyrrol-4-yl | |
| 1-Pyrazolyl | O | CH | 1-Phenylpyrrol-2-yl | |
| 1-Pyrazolyl | O | CH | 1-Phenylpyrrol-3-yl | |

TABLE 2-continued

Compounds I in which $R^1$ is a radical $OR^5$ ($R, R^3 = OCH_3, R^4 = H$).

| $R^5$ | X | Z | A | Phys. data m.p. [°C.] |
|---|---|---|---|---|
| 1-Pyrazolyl | O | CH | 1,4-Dimethylpyrrol-3-yl | |
| 1-Pyrazolyl | O | CH | 5-Methyl-1-phenyl-pyrrol-3-yl | |
| 1-Pyrazolyl | O | CH | 1,5-Dimethylpryyol-3-yl | |
| 1-Pyrazolyl | O | CH | 1,3-Dimethylpyrrol-4-yl | |
| 1-Pyrazolyl | O | CH | 1,5-Dimethylpyrrol-3-yl | |
| 1-Pyrazolyl | O | CH | 3-Methyl-1-phenyl-pyrrol-4-yl | |
| 1-Pyrazolyl | O | CH | 5-Methyl-1-phenyl-pyrrol-2-yl | |
| 1-Pyrazolyl | O | CH | 3,5-Dimethyl-1-phenyl-pyrrol-4-yl | |
| 1-Pyrazolyl | O | CH | 3-Methyl-1-phenyl-pyrrol-5-yl | |
| 1-Pyrazolyl | O | CH | 1,4-Dimethylpyrrol-5-yl | |
| 1-Pyrazolyl | O | CH | 1,3-Dimethylpyrrol-5-yl | |
| 1-Pyrazolyl | O | N | 2-Thienyl | |
| 1-Pyrazolyl | O | CH | 2-Thienyl | |
| 1-Pyrazolyl | S | CH | 2-Thienyl | |
| 1-Pyrazolyl | O | N | 3-Thienyl | |
| 1-Pyrazolyl | O | CH | 3-Thienyl | |
| 1-Pyrazolyl | S | CH | 3-Thienyl | |
| 1-Pyrazolyl | O | CH | 2,3-Dichloro-4-thienyl | |
| 1-Pyrazolyl | O | CH | 2,5-Dichloro-3-thienyl | |
| 1-Pyrazolyl | O | CH | 2-bromo-5-thienyl | |
| 1-Pyrazolyl | O | CH | 4-bromo-2-thienyl | |
| 1-Pyrazolyl | O | CH | 3-Methyl-2-thienyl | |
| 1-Pyrazolyl | O | CH | 2-chloro-5-thienyl | |
| 1-Pyrazolyl | O | CH | 2-Methyl-5-thienyl | |
| 1-Pyrazolyl | O | CH | 2-Nitro-5-thienyl | |
| 1-Pyrazolyl | O | N | Benzthien-2-yl | |
| 1-Pyrazolyl | O | CH | Benzthien-2-yl | |
| 1-Pyrazolyl | S | CH | Benzthien-2-yl | |
| 1-Pyrazolyl | O | N | Benzthien-3-yl | |
| 1-Pyrazolyl | O | CH | Benzthien-3-yl | |
| 1-Pyrazolyl | S | CH | Benzthien-3-yl | |
| 1-Pyrazolyl | O | N | 2-Furanyl | |
| 1-Pyrazolyl | O | CH | 2-Furanyl | |
| 1-Pyrazolyl | S | CH | 2-Furanyl | |
| 1-Pyrazolyl | O | N | 3-Furanyl | |
| 1-Pyrazolyl | O | CH | 3-Furanyl | |
| 1-Pyrazolyl | S | CH | 3-Furanyl | |
| 1-Pyrazolyl | O | CH | 2,3-Dichloro-4-furanyl | |
| 1-Pyrazolyl | O | CH | 2,5-Dichloro-3-furanyl | |
| 1-Pyrazolyl | O | CH | 2-bromo-5-furanyl | |
| 1-Pyrazolyl | O | CH | 4-bromo-2-furanyl | |
| 1-Pyrazolyl | O | CH | 3-Methyl-2-furanyl | |
| 1-Pyrazolyl | O | CH | 2-chloro-5-furanyl | |
| 1-Pyrazolyl | O | CH | 2-Methyl-5-furanyl | |
| 1-Pyrazolyl | O | CH | 2-Nitro-5-furanyl | |
| 1-Pyrazolyl | O | N | Benzofuran-2-yl | |
| 1-Pyrazolyl | O | CH | Benzofuran-2-yl | |
| 1-Pyrazolyl | S | CH | Benzofuran-2-yl | |
| 1-Pyrazolyl | O | N | Benzofuran-3-yl | |
| 1-Pyrazolyl | O | CH | Benzofuran-3-yl | |
| 1-Pyrazolyl | S | CH | Benzofuran-3-yl | |
| 1-Pyrazolyl | O | N | 1-Pyrazolyl | |
| 1-Pyrazolyl | O | CH | 1-Pyrazolyl | |
| 1-Pyrazolyl | S | CH | 1-Pyrazolyl | |
| 1-Pyrazolyl | O | N | 1-Methyl-pyrazol-3-yl | |
| 1-Pyrazolyl | O | CH | 1-Methyl-pyrazol-3-yl | |
| 1-Pyrazolyl | S | CH | 1-Methyl-pyrazol-3-yl | |
| 1-Pyrazolyl | O | N | 1-Methyl-pyrazol-4-yl | |
| 1-Pyrazolyl | O | CH | 1-Methyl-pyrazol-4-yl | |
| 1-Pyrazolyl | S | CH | 1-Methyl-pyrazol-4-yl | |
| 1-Pyrazolyl | O | N | 1-Methyl-pyrazol-5-yl | |
| 1-Pyrazolyl | O | CH | 1-Methyl-pyrazol-5-yl | |
| 1-Pyrazolyl | S | CH | 1-Methyl-pyrazol-5-yl | |
| 1-Pyrazolyl | O | CH | Benzpyrazol-1-yl | |
| 1-Pyrazolyl | O | CH | 1-Methyl-benzpyrazol-3-yl | |
| 1-Pyrazolyl | O | CH | 3,5-Dimethyl-pyrazol-1-yl | |
| 1-Pyrazolyl | O | CH | 3(5)-Methyl-pyrazol-1-yl | |

TABLE 2-continued

Compounds I in which R¹ is a radical OR⁵ (R, R³ = OCH₃, R⁴ = H).

| R⁵ | X | Z | A | Phys. data m.p. [°C.] |
|---|---|---|---|---|
| 1-Pyrazolyl | O | CH | 4-Methylpyrazol-1-yl | |
| 1-Pyrazolyl | O | CH | 4-chloropyrazol-1-yl | |
| 1-Pyrazolyl | O | CH | 4-bromopyrazol-1-yl | |
| 1-Pyrazolyl | O | CH | 4-Phenylpyrazol-1-yl | |
| 1-Pyrazolyl | O | CH | 3,4,5-Trimethyl-pyrazol-1-yl | |
| 1-Pyrazolyl | O | CH | 4-chloro-3,5-dimethyl-pyrazol-1-yl | |
| 1-Pyrazolyl | O | CH | 4-Isopropylpyrazol-1-yl | |
| 1-Pyrazolyl | O | CH | 3(5)-Phenylpyrazol-1-yl | |
| 1-Pyrazolyl | O | CH | 3(5)-Methyl-5(3)-phenyl-pyrazol-1-yl | |
| 1-Pyrazolyl | O | CH | 3,5-Bistrifluoromethyl-pyrazol-1-yl | |
| 1-Pyrazolyl | O | CH | 4-Nitropyrazol-1-yl | |
| 1-Pyrazolyl | O | CH | 1-Phenylpyrazol-4-yl | |
| 1-Pyrazolyl | O | CH | 1,3,5-Trimethyl-pyrazol-4-yl | |
| 1-Pyrazolyl | O | CH | 1-Phenylpyrazol-5-yl | |
| 1-Pyrazolyl | O | CH | 1-Phenylpyrazol-3-yl | |
| 1-Pyrazolyl | O | CH | 1,4-Dimethylpyrazol-3-yl | |
| 1-Pyrazolyl | O | CH | 5-Methyl-1-phenyl-pyrazol-3-yl | |
| 1-Pyrazolyl | O | CH | 1,5-Dimethylpyrazol-3-yl | |
| 1-Pyrazolyl | O | CH | 1,3-Dimethylpyrazol-4-yl | |
| 1-Pyrazolyl | O | CH | 1,5-Dimethylpyrazol-4-yl | |
| 1-Pyrazolyl | O | CH | 3-Methyl-1-phenyl-pyrazol-4-yl | |
| 1-Pyrazolyl | O | CH | 5-Methyl-1-phenyl-pyrazol-4-yl | |
| 1-Pyrazolyl | O | CH | 3,5-Dimethyl-1-phenyl-pyrazol-4-yl | |
| 1-Pyrazolyl | O | CH | 3-Methyl-1-phenyl-pyrazol-5-yl | |
| 1-Pyrazolyl | O | CH | 1,4-Dimethylpyrazol-5-yl | |
| 1-Pyrazolyl | O | CH | 1,3-Dimethylpyrazol-5-yl | |
| 1-Pyrazolyl | O | N | 1-Imidazolyl | |
| 1-Pyrazolyl | O | CH | 1-Imidazolyl | |
| 1-Pyrazolyl | S | CH | 1-Imidazolyl | |
| 1-Pyrazolyl | O | N | 1-Methyl-imidazol-2-yl | |
| 1-Pyrazolyl | O | CH | 1-Methyl-imidazol-2-yl | |
| 1-Pyrazolyl | S | CH | 1-Methyl-imidazol-2-yl | |
| 1-Pyrazolyl | O | N | 1-Methyl-imidazol-4-yl | |
| 1-Pyrazolyl | O | CH | 1-Methyl-imidazol-4-yl | |
| 1-Pyrazolyl | S | CH | 1-Methyl-imidazol-4-yl | |
| 1-Pyrazolyl | O | N | 1-Methyl-imidazol-5-yl | |
| 1-Pyrazolyl | O | CH | 1-Methyl-imidazol-5-yl | |
| 1-Pyrazolyl | S | CH | 1-Methyl-imidazol-5-yl | |
| 1-Pyrazolyl | O | CH | Benzimidazol-1-yl | |
| 1-Pyrazolyl | O | CH | 1-Methyl-benzimidazol-2-yl | |
| 1-Pyrazolyl | O | CH | 4,5-Dimethylimidazol-1-yl | |
| 1-Pyrazolyl | O | CH | 2-Phenylimidazol-1-yl | |
| 1-Pyrazolyl | O | CH | 4,5-Dichloroimidazol-1-yl | |
| 1-Pyrazolyl | O | CH | 2,4,5-Trichloro-imidazol-1-yl | |
| 1-Pyrazolyl | O | CH | 2-Methyl-4,5-dichloro-imidazol-1-yl | |
| 1-Pyrazolyl | O | CH | 2-Methyl-4,5-dibromo-imidazol-1-yl | |
| 1-Pyrazolyl | O | CH | 4(5)-chloro-5(4)-methyl-imidazol-1-yl | |
| 1-Pyrazolyl | O | CH | 4(5)-Nitroimidazol-1-yl | |
| 1-Pyrazolyl | O | CH | 1,4-Dimethyl-imidazol-5-yl | |
| 1-Pyrazolyl | O | CH | 1-Methyl-5-nitro-imidazol-2-yl | |
| 1-Pyrazolyl | O | CH | 1-Phenylimidazol-5-yl | |
| 1-Pyrazolyl | O | N | 1,2,3-Triazol-1-yl | |
| 1-Pyrazolyl | O | CH | 1,2,3-Triazol-1-yl | |
| 1-Pyrazolyl | S | CH | 1,2,3-Triazol-1-yl | |
| 1-Pyrazolyl | O | N | 1-Methyl-1,2,3-triazol-4-yl | |
| 1-Pyrazolyl | O | CH | 1-Methyl-1,2,3-triazol-4-yl | |
| 1-Pyrazolyl | S | CH | 1-Methyl-1,2,3-triazol-4-yl | |
| 1-Pyrazolyl | O | N | 1-Methyl-1,2,3-triazol-5-yl | |
| 1-Pyrazolyl | O | CH | 1-Methyl-1,2,3-triazol-5-yl | |
| 1-Pyrazolyl | S | CH | 1-Methyl-1,2,3-triazol-5-yl | |
| 1-Pyrazolyl | O | CH | Benz-1,2,3-triazol-1-yl | |
| 1-Pyrazolyl | O | CH | 4,5-Dimethyl-1,2,3-triazol-1-yl | |
| 1-Pyrazolyl | O | CH | 4(5)-Phenyl-1,2,3-triazol-1-yl | |
| 1-Pyrazolyl | O | CH | 1-Phenyl-1,2,3-triazol-4-yl | |
| 1-Pyrazolyl | O | CH | 5-Methyl-1-phenyl-1,2,3-triazol-4-yl | |
| 1-Pyrazolyl | O | N | 1,2,4-Triazol-1-yl | |

TABLE 2-continued

Compounds I in which R¹ is a radical OR⁵ (R, R³ = OCH₃, R⁴ = H).

| R⁵ | X | Z | A | Phys. data m.p. [°C.] |
|---|---|---|---|---|
| 1-Pyrazolyl | O | CH | 1,2,4-Triazol-1-yl | |
| 1-Pyrazolyl | S | CH | 1,2,4-Triazol-1-yl | |
| 1-Pyrazolyl | O | N | 1-Methyl-1,2,4-triazol-3-yl | |
| 1-Pyrazolyl | O | CH | 1-Methyl-1,2,4-triazol-3-yl | |
| 1-Pyrazolyl | S | CH | 1-Methyl-1,2,4-triazol-3-yl | |
| 1-Pyrazolyl | O | N | 1-Methyl-1,2,4-triazol-5-yl | |
| 1-Pyrazolyl | O | CH | 1-Methyl-1,2,4-triazol-5-yl | |
| 1-Pyrazolyl | S | CH | 1-Methyl-1,2,4-triazol-5-yl | |
| 1-Pyrazolyl | O | CH | 3(5)-Phenyl-1,2,4-triazol-1-yl | |
| 1-Pyrazolyl | O | CH | 3,5-Dimethyl-1,2,4-triazol-1-yl | |
| 1-Pyrazolyl | O | CH | 5-Methyl-1-phenyl-1,2,4-triazol-3-yl | |
| 1-Pyrazolyl | O | N | 1-Tetrazolyl | |
| 1-Pyrazolyl | O | CH | 1-Tetrazolyl | |
| 1-Pyrazolyl | S | CH | 1-Tetrazolyl | |
| 1-Pyrazolyl | O | N | 1-Methyl-tetrazol-5-yl | |
| 1-Pyrazolyl | O | CH | 1-Methyl-tetrazol-5-yl | |
| 1-Pyrazolyl | S | CH | 1-Methyl-tetrazol-5-yl | |
| 1-Pyrazolyl | O | N | 2-Oxazolyl | |
| 1-Pyrazolyl | O | CH | 2-Oxazolyl | |
| 1-Pyrazolyl | S | CH | 2-Oxazolyl | |
| 1-Pyrazolyl | O | N | 4-Oxazolyl | |
| 1-Pyrazolyl | O | CH | 4-Oxazolyl | |
| 1-Pyrazolyl | S | CH | 4-Oxazolyl | |
| 1-Pyrazolyl | O | N | 5-Oxazolyl | |
| 1-Pyrazolyl | O | CH | 5-Oxazolyl | |
| 1-Pyrazolyl | S | CH | 5-Oxazolyl | |
| 1-Pyrazolyl | O | CH | 2-Methyloxazol-4-yl | |
| 1-Pyrazolyl | O | CH | Benzoxazol-2-yl | |
| 1-Pyrazolyl | O | N | Isoxazol-3-yl | |
| 1-Pyrazolyl | O | CH | Isoxazol-3-yl | |
| 1-Pyrazolyl | S | CH | Isoxazol-3-yl | |
| 1-Pyrazolyl | O | N | Isoxazol-4-yl | |
| 1-Pyrazolyl | O | CH | Isoxazol-4-yl | |
| 1-Pyrazolyl | S | CH | Isoxazol-4-yl | |
| 1-Pyrazolyl | O | N | Isoxazol-5-yl | |
| 1-Pyrazolyl | O | CH | Isoxazol-5-yl | |
| 1-Pyrazolyl | S | CH | Isoxazol-5-yl | |
| 1-Pyrazolyl | O | CH | Benzisoxazol-3-yl | |
| 1-Pyrazolyl | O | CH | 3-Methylisoxazol-5-yl | |
| 1-Pyrazolyl | O | CH | 3-Isopropylisoxazol-5-yl | |
| 1-Pyrazolyl | O | CH | 3-Phenylisoxazol-5-yl | |
| 1-Pyrazolyl | O | CH | 3-Methyl-4-chloro-isoxazol-5-yl | |
| 1-Pyrazolyl | O | CH | 3-Methylisoxazol-4-yl | |
| 1-Pyrazolyl | O | CH | 3,5-Dimethyl-isoxazol-4-yl | |
| 1-Pyrazolyl | O | N | 2-Thiazolyl | |
| 1-Pyrazolyl | O | CH | 2-Thiazolyl | |
| 1-Pyrazolyl | S | CH | 2-Thiazolyl | |
| 1-Pyrazolyl | O | N | 4-Thiazolyl | |
| 1-Pyrazolyl | O | CH | 4-Thiazolyl | |
| 1-Pyrazolyl | S | CH | 4-Thiazolyl | |
| 1-Pyrazolyl | O | N | 5-Thiazolyl | |
| 1-Pyrazolyl | O | CH | 5-Thiazolyl | |
| 1-Pyrazolyl | S | CH | 5-Thiazolyl | |
| 1-Pyrazolyl | O | CH | Benzthiazol-2-yl | |
| 1-Pyrazolyl | O | CH | 2-Methylthiazol-4-yl | |
| 1-Pyrazolyl | O | CH | 2-Phenylthiazol-4-yl | |
| 1-Pyrazolyl | O | CH | 2-Benzylthiazol-4-yl | |
| 1-Pyrazolyl | O | CH | 5-chloro-2-phenyl-thiazol-4-yl | |
| 1-Pyrazolyl | O | CH | 4-Methylthiazol-2-yl | |
| 1-Pyrazolyl | O | CH | 5-Methylthiazol-2-yl | |
| 1-Pyrazolyl | O | CH | 4-Phenylthiazol-2-yl | |
| 1-Pyrazolyl | O | CH | 4-Methylthiazol-5-yl | |
| 1-Pyrazolyl | O | CH | 2-Methylthiazol-5-yl | |
| 1-Pyrazolyl | O | CH | 2-Phenylthiazol-5-yl | |
| 1-Pyrazolyl | O | N | Isothiazol-3-yl | |
| 1-Pyrazolyl | O | CH | Isothiazol-3-yl | |
| 1-Pyrazolyl | S | CH | Isothiazol-3-yl | |

TABLE 2-continued

Compounds I in which $R^1$ is a radical $OR^5$ (R, $R^3$ = $OCH_3$, $R^4$ = H).

| $R^5$ | X | Z | A | Phys. data m.p. [°C.] |
|---|---|---|---|---|
| 1-Pyrazolyl | O | N | Isothiazol-4-yl | |
| 1-Pyrazolyl | O | CH | Isothiazol-4-yl | |
| 1-Pyrazolyl | S | CH | Isothiazol-4-yl | |
| 1-Pyrazolyl | O | N | Isothiazol-5-yl | |
| 1-Pyrazolyl | O | CH | Isothiazol-5-yl | |
| 1-Pyrazolyl | S | CH | Isothiazol-5-yl | |
| 1-Pyrazolyl | O | CH | Benzisothiazol-3-yl | |
| 1-Pyrazolyl | O | N | 1,2,3-Thiadiazol-4-yl | |
| 1-Pyrazolyl | O | CH | 1,2,3-Thiadiazol-4-yl | |
| 1-Pyrazolyl | S | CH | 1,2,3-Thiadiazol-4-yl | |
| 1-Pyrazolyl | O | N | 1,2,3-Thiadiazol-5-yl | |
| 1-Pyrazolyl | O | CH | 1,2,3-Thiadiazol-5-yl | |
| 1-Pyrazolyl | S | CH | 1,2,3-Thiadiazol-5-yl | |
| 1-Pyrazolyl | O | N | 1,3,4-Thiadiazol-2-yl | |
| 1-Pyrazolyl | O | CH | 1,3,4-Thiadiazol-2-yl | |
| 1-Pyrazolyl | S | CH | 1,3,4-Thiadiazol-2-yl | |
| 1-Pyrazolyl | O | N | 1,3,4-Thiadiazol-5-yl | |
| 1-Pyrazolyl | O | CH | 1,3,4-Thiadiazol-5-yl | |
| 1-Pyrazolyl | S | CH | 1,3,4-Thiadiazol-5-yl | |
| 1-Pyrazolyl | O | CH | 5-Methyl-1,3,4-thiadiazol-2-yl | |
| 1-Pyrazolyl | O | CH | 5-Phenyl-1,3,4-thiadiazol-2-yl | |
| 1-Pyrazolyl | O | N | 1,2,3-Oxadiazol-4-yl | |
| 1-Pyrazolyl | O | CH | 1,2,3-Oxadiazol-4-yl | |
| 1-Pyrazolyl | S | CH | 1,2,3-Oxadiazol-4-yl | |
| 1-Pyrazolyl | O | N | 1,2,3-Oxadiazol-5-yl | |
| 1-Pyrazolyl | O | CH | 1,2,3-Oxadiazol-5-yl | |
| 1-Pyrazolyl | S | CH | 1,2,3-Oxadiazol-5-yl | |
| 1-Pyrazolyl | O | N | 1,2,4-Oxadiazol-3-yl | |
| 1-Pyrazolyl | O | CH | 1,2,4-Oxadiazol-3-yl | |
| 1-Pyrazolyl | S | CH | 1,2,4-Oxadiazol-3-yl | |
| 1-Pyrazolyl | O | N | 1,2,4-Oxadiazol-5-yl | |
| 1-Pyrazolyl | O | CH | 1,2,4-Oxadiazol-5-yl | |
| 1-Pyrazolyl | S | CH | 1,2,4-Oxadiazol-5-yl | |
| 1-Pyrazolyl | O | N | 1,2,3,4-Thiatriazol-5-yl | |
| 1-Pyrazolyl | O | CH | 1,2,3,4-Thiatriazol-5-yl | |
| 1-Pyrazolyl | S | CH | 1,2,3,4-Thiatriazol-5-yl | |
| 1-Pyrazolyl | O | N | 2-Pyridyl | |
| 1-Pyrazolyl | O | CH | 2-Pyridyl | |
| 1-Pyrazolyl | S | CH | 2-Pyridyl | |
| 1-Pyrazolyl | O | N | 3-Pyridyl | |
| 1-Pyrazolyl | O | CH | 3-Pyridyl | |
| 1-Pyrazolyl | S | CH | 3-Pyridyl | |
| 1-Pyrazolyl | O | N | 4-Pyridyl | |
| 1-Pyrazolyl | O | CH | 4-Pyridyl | |
| 1-Pyrazolyl | S | CH | 4-Pyridyl | |
| 1-Pyrazolyl | O | CH | 6-Methyl-2-pyridyl | |
| 1-Pyrazolyl | O | CH | 3-chloro-5-pyridyl | |
| 1-Pyrazolyl | O | CH | 5-chloro-2-pyridyl | |
| 1-Pyrazolyl | O | N | 2-Naphthyl | |
| 1-Pyrazolyl | O | CH | 2-Naphthyl | |
| 1-Pyrazolyl | S | CH | 2-Naphthyl | |
| 1-Pyrazolyl | O | N | 1-Naphthyl | |
| 1-Pyrazolyl | O | CH | 1-Naphthyl | |
| 1-Pyrazolyl | S | CH | 1-Naphthyl | |
| 1-Pyrazolyl | O | CH | 2-Methyl-1-naphthyl | |
| 1-Pyrazolyl | O | CH | 2-Methoxy-1-naphthyl | |
| 1-Pyrazolyl | O | CH | 1-chloro-4-naphthyl | |
| 1-Pyrazolyl | O | N | 2-quinolinyl | |
| 1-Pyrazolyl | O | CH | 2-quinolinyl | |
| 1-Pyrazolyl | S | CH | 2-quinolinyl | |
| 1-Pyrazolyl | O | N | 4-quinolinyl | |
| 1-Pyrazolyl | O | CH | 4-quinolinyl | |
| 1-Pyrazolyl | S | CH | 4-quinolinyl | |
| 1-Pyrazolyl | O | CH | 2-chloro-quinolin-2-yl | |
| 1-Pyrazolyl | O | CH | 2,6-Dichloro-quinolin-3-yl | |
| 1-Pyrazolyl | O | CH | 2-chloro-6-methyl-quinolin-3-yl | |
| 1-Imidazolyl | O | CH | 1-Pyrrolyl | |

TABLE 2-continued

Compounds I in which $R^1$ is a radical $OR^5$ (R, $R^3$ = $OCH_3$, $R^4$ = H).

| $R^5$ | X | Z | A | Phys. data m.p. [°C.] |
|---|---|---|---|---|
| 1-Imidazolyl | O | CH | 1-Indolyl | |
| 1-Imidazolyl | O | CH | 2-Thienyl | |
| 1-Imidazolyl | O | CH | 3-Thienyl | |
| 1-Imidazolyl | O | CH | 2-bromo-5-thienyl | |
| 1-Imidazolyl | O | CH | 3-Methyl-2-thienyl | |
| 1-Imidazolyl | O | CH | 2-chloro-5-thienyl | |
| 1-Imidazolyl | O | CH | Benzthien-2-yl | |
| 1-Imidazolyl | O | CH | Benzthien-3-yl | |
| 1-Imidazolyl | O | CH | 2-Furanyl | |
| 1-Imidazolyl | O | CH | 3-Furanyl | |
| 1-Imidazolyl | O | CH | Benzofuran-2-yl | |
| 1-Imidazolyl | O | CH | 1-Pyrazolyl | |
| 1-Imidazolyl | O | CH | 1-Methyl-pyrazol-3-yl | |
| 1-Imidazolyl | O | CH | Benzpyrazol-1-yl | |
| 1-Imidazolyl | O | CH | 1-Imidazolyl | |
| 1-Imidazolyl | O | CH | 1-Methyl-imidazol-4-yl | |
| 1-Imidazolyl | O | CH | Benzimidazol-1-yl | |
| 1-Imidazolyl | O | CH | 1,2,3-Triazol-1-yl | |
| 1-Imidazolyl | O | N | 1-Methyl-1,2,3-triazol-4-yl | |
| 1-Imidazolyl | O | CH | Benz-1,2,3-triazol-1-yl | |
| 1-Imidazolyl | O | CH | 1,2,4-Triazol-1-yl | |
| 1-Imidazolyl | O | CH | 1-Methyl-1,2,4-triazol-3-yl | |
| 1-Imidazolyl | O | CH | 1-Tetrazolyl | |
| 1-Imidazolyl | O | CH | 2-Oxazolyl | |
| 1-Imidazolyl | O | CH | 4-Oxazolyl | |
| 1-Imidazolyl | O | CH | 5-Oxazolyl | |
| 1-Imidazolyl | O | CH | Benzoxazol-2-yl | |
| 1-Imidazolyl | O | CH | Isoxazol-3-yl | |
| 1-Imidazolyl | O | CH | Isoxazol-4-yl | |
| 1-Imidazolyl | O | CH | Isoxazol-5-yl | |
| 1-Imidazolyl | O | CH | Benzisoxazol-3-yl | |
| 1-Imidazolyl | O | CH | 2-Thiazolyl | |
| 1-Imidazolyl | O | CH | 4-Thiazolyl | |
| 1-Imidazolyl | O | CH | 5-Thiazolyl | |
| 1-Imidazolyl | O | CH | Benzthiazol-2-yl | |
| 1-Imidazolyl | O | CH | Isothiazol-3-yl | |
| 1-Imidazolyl | O | CH | Isothiazol-4-yl | |
| 1-Imidazolyl | O | CH | Isothiazol-5-yl | |
| 1-Imidazolyl | O | CH | Benzisothiazol-3-yl | |
| 1-Imidazolyl | O | CH | 1,2,3-Thiadiazol-4-yl | |
| 1-Imidazolyl | O | CH | 1,2,3-Thiadiazol-5-yl | |
| 1-Imidazolyl | O | CH | 1,3,4-Thiadiazol-2-yl | |
| 1-Imidazolyl | O | CH | 1,3,4-Thiadiazol-5-yl | |
| 1-Imidazolyl | O | CH | 1,2,3-Oxadiazol-4-yl | |
| 1-Imidazolyl | O | CH | 1,2,3-Oxadiazol-5-yl | |
| 1-Imidazolyl | O | CH | 1,2,4-Oxadiazol-3-yl | |
| 1-Imidazolyl | O | CH | 1,2,4-Oxadiazol-5-yl | |
| 1-Imidazolyl | O | CH | 1,2,3,4-Thiatriazol-5-yl | |
| 1-Imidazolyl | O | CH | 2-Pyridyl | |
| 1-Imidazolyl | O | CH | 3-Pyridyl | |
| 1-Imidazolyl | O | CH | 4-Pyridyl | |
| 1-Imidazolyl | O | CH | 2-Naphthyl | |
| 1-Imidazolyl | O | CH | 1-Naphthyl | |
| 1-Imidazolyl | O | CH | 2-quinolinyl | |
| 1-Imidazolyl | O | CH | 4-quinolinyl | |
| 1-Imidazolyl | O | CH | 1-Pyrrolyl | |
| 1-Imidazolyl | O | CH | 1-1-Indolyl | |
| 1-Imidazolyl | O | CH | 2-Thienyl | |
| 1-Imidazolyl | O | CH | 3-Thienyl | |
| 1-Imidazolyl | O | CH | 2-bromo-5-thienyl | |
| 1-Imidazolyl | O | CH | 3-Methyl-2-thienyl | |
| 1-Imidazolyl | O | CH | 2-chloro-5-thienyl | |
| 1-Imidazolyl | O | CH | Benzthien-2-yl | |
| 1-Imidazolyl | O | CH | Benzthien-3-yl | |
| 1-Imidazolyl | O | CH | 2-Furanyl | |
| 1-Imidazolyl | O | CH | 3-Furanyl | |
| 1-Imidazolyl | O | CH | Benzofuran-2-yl | |

TABLE 2-continued

Compounds I in which $R^1$ is a radical $OR^5$ ($R$, $R^3 = OCH_3$, $R^4 = H$).

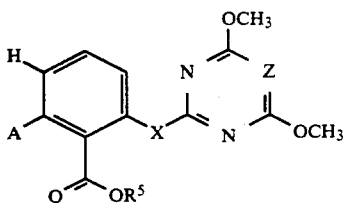

| $R^5$ | X | Z | A | Phys. data m.p. [°C.] |
|---|---|---|---|---|
| 1-Imidazolyl | O | CH | 1-Pyrazolyl | |
| 1-Imidazolyl | O | CH | 1-Methyl-pyrazol-3-yl | |
| 1-Imidazolyl | O | CH | Benzpyrazol-1-yl | |
| 1-Imidazolyl | O | CH | 1-Imidazolyl | |
| 1-Imidazolyl | O | CH | 1-Methyl-imidazol-4-yl | |
| 1-Imidazolyl | O | CH | Benzimidazol-1-yl | |
| 1-Imidazolyl | O | CH | 1,2,3-Triazol-1-yl | |
| 1-Imidazolyl | O | N | 1-Methyl-1,2,3-triazol-4-yl | |
| 1-Imidazolyl | O | CH | Benz-1,2,3-triazol-1-yl | |
| 1-Imidazolyl | O | CH | 1,2,4-Triazol-1-yl | |
| 1-Imidazolyl | O | CH | 1-Methyl-1,2,4-triazol-3-yl | |
| 1-Imidazolyl | O | CH | 1-Tetrazolyl | |
| 1-Imidazolyl | O | CH | 2-Oxazolyl | |
| 1-Imidazolyl | O | CH | 4-Oxazolyl | |
| 1-Imidazolyl | O | CH | 5-Oxazolyl | |
| 1-Imidazolyl | O | CH | Benzoxazol-2-yl | |
| 1-Imidazolyl | O | CH | Isoxazol-3-yl | |
| 1-Imidazolyl | O | CH | Isoxazol-4-yl | |
| 1-Imidazolyl | O | CH | Isoxazol-5-yl | |
| 1-Imidazolyl | O | CH | Benzisoxazol-3-yl | |
| 1-Imidazolyl | O | CH | 2-Thiazolyl | |
| 1-Imidazolyl | O | CH | 4-Thiazolyl | |
| 1-Imidazolyl | O | CH | 5-Thiazolyl | |
| 1-Imidazolyl | O | CH | Benzthiazol-2-yl | |
| 1-Imidazolyl | O | CH | Isothiazol-3-yl | |
| 1-Imidazolyl | O | CH | Isothiazol-4-yl | |
| 1-Imidazolyl | O | CH | Isothiazol-5-yl | |
| 1-Imidazolyl | O | CH | Benzisothiazol-3-yl | |
| 1-Imidazolyl | O | CH | 1,2,3-Thiadiazol-4-yl | |
| 1-Imidazolyl | O | CH | 1,2,3-Thiadiazol-5-yl | |
| 1-Imidazolyl | O | CH | 1,3,4-Thiadiazol-2-yl | |
| 1-Imidazolyl | O | CH | 1,3,4-Thiadiazol-5-yl | |
| 1-Imidazolyl | O | CH | 1,2,3-Oxadiazol-4-yl | |
| 1-Imidazolyl | O | CH | 1,2,3-Oxadiazol-5-yl | |
| 1-Imidazolyl | O | CH | 1,2,4-Oxadiazol-3-yl | |
| 1-Imidazolyl | O | CH | 1,2,4-Oxadiazol-5-yl | |
| 1-Imidazolyl | O | CH | 1,2,3,4-Thiatriazol-5-yl | |
| 1-Imidazolyl | O | CH | 2-Pyridyl | |
| 1-Imidazolyl | O | CH | 3-Pyridyl | |
| 1-Imidazolyl | O | CH | 4-Pyridyl | |
| 1-Imidazolyl | O | CH | 2-Naphthyl | |
| 1-Imidazolyl | O | CH | 1-Naphthyl | |
| 1-Imidazolyl | O | CH | 2-quinolinyl | |
| 1-Imidazolyl | O | CH | 4-quinolinyl | |
| 1-Pyrrolyl | O | CH | 1-Pyrrolyl | |
| 1-Pyrrolyl | O | CH | 1-Indolyl | |
| 1-Pyrrolyl | O | CH | 2-Thienyl | |
| 1-Pyrrolyl | O | CH | 3-Thienyl | |
| 1-Pyrrolyl | O | CH | 2-bromo-5-thienyl | |
| 1-Pyrrolyl | O | CH | 3-Methyl-2-thienyl | |
| 1-Pyrrolyl | O | CH | 2-chloro-5-thienyl | |
| 1-Pyrrolyl | O | CH | Benzthien-2-yl | |
| 1-Pyrrolyl | O | CH | Benzthien-3-yl | |
| 1-Pyrrolyl | O | CH | 2-Furanyl | |
| 1-Pyrrolyl | O | CH | 3-Furanyl | |
| 1-Pyrrolyl | O | CH | Benzofuran-2-yl | |
| 1-Pyrrolyl | O | CH | 1-Pyrazolyl | |
| 1-Pyrrolyl | O | CH | 1-Methyl-pyrazol-3-yl | |
| 1-Pyrrolyl | O | CH | Benzpyrazol-1-yl | |
| 1-Pyrrolyl | O | CH | 1-Imidazolyl | |
| 1-Pyrrolyl | O | CH | 1-Methyl-imidazol-4-yl | |
| 1-Pyrrolyl | O | CH | Benzimidazol-1-yl | |
| 1-Pyrrolyl | O | CH | 1,2,3-Triazol-1-yl | |
| 1-Pyrrolyl | O | N | 1-Methyl-1,2,3-triazol-4-yl | |
| 1-Pyrrolyl | O | CH | Benz-1,2,3-triazol-1-yl | |
| 1-Pyrrolyl | O | CH | 1,2,4-Triazol-1-yl | |
| 1-Pyrrolyl | O | CH | 1-Methyl-1,2,4-triazol-3-yl | |

TABLE 2-continued

Compounds I in which $R^1$ is a radical $OR^5$ (R, $R^3$ = $OCH_3$, $R^4$ = H).

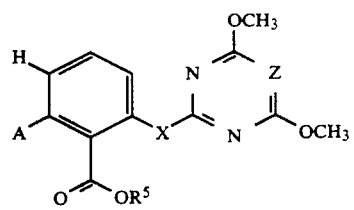

| $R^5$ | X | Z | A | Phys. data m.p. [°C.] |
|---|---|---|---|---|
| 1-Pyrrolyl | O | CH | 1-Tetrazolyl | |
| 1-Pyrrolyl | O | CH | 2-Oxazolyl | |
| 1-Pyrrolyl | O | CH | 4-Oxazolyl | |
| 1-Pyrrolyl | O | CH | 5-Oxazolyl | |
| 1-Pyrrolyl | O | CH | Benzoxazol-2-yl | |
| 1-Pyrrolyl | O | CH | Isoxazol-3-yl | |
| 1-Pyrrolyl | O | CH | Isoxazol-4-yl | |
| 1-Pyrrolyl | O | CH | Isoxazol-5-yl | |
| 1-Pyrrolyl | O | CH | Benzisoxazol-3-yl | |
| 1-Pyrrolyl | O | CH | 2-Thiazolyl | |
| 1-Pyrrolyl | O | CH | 4-Thiazolyl | |
| 1-Pyrrolyl | O | CH | 5-Thiazolyl | |
| 1-Pyrrolyl | O | CH | Benzthiazol-2-yl | |
| 1-Pyrrolyl | O | CH | Isothiazol-3-yl | |
| 1-Pyrrolyl | O | CH | Isothiazol-4-yl | |
| 1-Pyrrolyl | O | CH | Isothiazol-5-yl | |
| 1-Pyrrolyl | O | CH | Benzisothiazol-3-yl | |
| 1-Pyrrolyl | O | CH | 1,2,3-Thiadiazol-4-yl | |
| 1-Pyrrolyl | O | CH | 1,2,3-Thiadiazol-5-yl | |
| 1-Pyrrolyl | O | CH | 1,3,4-Thiadiazol-2-yl | |
| 1-Pyrrolyl | O | CH | 1,3,4-Thiadiazol-5-yl | |
| 1-Pyrrolyl | O | CH | 1,2,3-Oxadiazol-4-yl | |
| 1-Pyrrolyl | O | CH | 1,2,3-Oxadiazol-5-yl | |
| 1-Pyrrolyl | O | CH | 1,2,4-Oxadiazol-3-yl | |
| 1-Pyrrolyl | O | CH | 1,2,4-Oxadiazol-5-yl | |
| 1-Pyrrolyl | O | CH | 1,2,3,4-Thiatriazol-5-yl | |
| 1-Pyrrolyl | O | CH | 2-Pyridyl | |
| 1-Pyrrolyl | O | CH | 3-Pyridyl | |
| 1-Pyrrolyl | O | CH | 4-Pyridyl | |
| 1-Pyrrolyl | O | CH | 2-Naphthyl | |
| 1-Pyrrolyl | O | CH | 1-Naphthyl | |
| 1-Pyrrolyl | O | CH | 2-quinolinyl | |
| 1-Pyrrolyl | O | CH | 4-quinolinyl | |
| $CH_2P(O)(OC_2H_5)_2$ | O | CH | 1-Pyrrolyl | |
| $CH_2P(O)(OC_2H_5)_2$ | O | CH | 1-Indolyl | |
| $CH_2P(O)(OC_2H_5)_2$ | O | CH | 2-Thienyl | |
| $CH_2P(O)(OC_2H_5)_2$ | O | CH | 3-Thienyl | |
| $CH_2P(O)(OC_2H_5)_2$ | O | CH | 2-bromo-5-thienyl | |
| $CH_2P(O)(OC_2H_5)_2$ | O | CH | 3-Methyl-2-thienyl | |
| $CH_2P(O)(OC_2H_5)_2$ | O | CH | 2-chloro-5-thienyl | |
| $CH_2P(O)(OC_2H_5)_2$ | O | CH | Benzthien-2-yl | |
| $CH_2P(O)(OC_2H_5)_2$ | O | CH | Benzthien-3-yl | |
| $CH_2P(O)(OC_2H_5)_2$ | O | CH | 2-Furanyl | |
| $CH_2P(O)(OC_2H_5)_2$ | O | CH | 3-Furanyl | |
| $CH_2P(O)(OC_2H_5)_2$ | O | CH | Benzofuran-2-yl | |
| $CH_2P(O)(OC_2H_5)_2$ | O | CH | 1-Pyrazolyl | |
| $CH_2P(O)(OC_2H_5)_2$ | O | CH | 1-Methyl-pyrazol-3-yl | |
| $CH_2P(O)(OC_2H_5)_2$ | O | CH | Benzpyrazol-1-yl | |
| $CH_2P(O)(OC_2H_5)_2$ | O | CH | 1-Imidazolyl | |
| $CH_2P(O)(OC_2H_5)_2$ | O | CH | 1-Methyl-imidazol-4-yl | |
| $CH_2P(O)(OC_2H_5)_2$ | O | CH | Benzimidazol-1-yl | |
| $CH_2P(O)(OC_2H_5)_2$ | O | CH | 1,2,3-Triazol-1-yl | |
| $CH_2P(O)(OC_2H_5)_2$ | O | N | 1-Methyl-1,2,3-triazol-4-yl | |
| $CH_2P(O)(OC_2H_5)_2$ | O | CH | Benz-1,2,3-triazol-1-yl | |
| $CH_2P(O)(OC_2H_5)_2$ | O | CH | 1,2,4-Triazol-1-yl | |
| $CH_2P(O)(OC_2H_5)_2$ | O | CH | 1-Methyl-1,2,3-triazol-3-yl | |
| $CH_2P(O)(OC_2H_5)_2$ | O | CH | 1-Tetrazolyl | |
| $CH_2P(O)(OC_2H_5)_2$ | O | CH | 2-Oxazolyl | |
| $CH_2P(O)(OC_2H_5)_2$ | O | CH | 4-Oxazolyl | |
| $CH_2P(O)(OC_2H_5)_2$ | O | CH | 5-Oxazolyl | |
| $CH_2P(O)(OC_2H_5)_2$ | O | CH | Benzoxazol-2-yl | |
| $CH_2P(O)(OC_2H_5)_2$ | O | CH | Isoxazol-3-yl | |
| $CH_2P(O)(OC_2H_5)_2$ | O | CH | Isoxazol-4-yl | |
| $CH_2P(O)(OC_2H_5)_2$ | O | CH | Isoxazol-5-yl | |
| $CH_2P(O)(OC_2H_5)_2$ | O | CH | Benzisoxazol-3-yl | |
| $CH_2P(O)(OC_2H_5)_2$ | O | CH | 2-Thiazolyl | |
| $CH_2P(O)(OC_2H_5)_2$ | O | CH | 4-Thiazolyl | |

TABLE 2-continued

Compounds I in which $R^1$ is a radical $OR^5$ (R, $R^3$ = $OCH_3$, $R^4$ = H).

| $R^5$ | X | Z | A | Phys. data m.p. [°C.] |
|---|---|---|---|---|
| $CH_2P(O)(OC_2H_5)_2$ | O | CH | 5-Thiazolyl | |
| $CH_2P(O)(OC_2H_5)_2$ | O | CH | Benzthiazol-2-yl | |
| $CH_2P(O)(OC_2H_5)_2$ | O | CH | Isothiazol-3-yl | |
| $CH_2P(O)(OC_2H_5)_2$ | O | CH | Isothiazol-4-yl | |
| $CH_2P(O)(OC_2H_5)_2$ | O | CH | Isothiazol-5-yl | |
| $CH_2P(O)(OC_2H_5)_2$ | O | CH | Benzisothiazol-3-yl | |
| $CH_2P(O)(OC_2H_5)_2$ | O | CH | 1,2,3-Thiadiazol-4-yl | |
| $CH_2P(O)(OC_2H_5)_2$ | O | CH | 1,2,3-Thiadiazol-5-yl | |
| $CH_2P(O)(OC_2H_5)_2$ | O | CH | 1,3,4-Thiadiazol-2-yl | |
| $CH_2P(O)(OC_2H_5)_2$ | O | CH | 1,3,4-Thiadiazol-5-yl | |
| $CH_2P(O)(OC_2H_5)_2$ | O | CH | 1,2,3-Oxadiazol-4-yl | |
| $CH_2P(O)(OC_2H_5)_2$ | O | CH | 1,2,3-Oxadiazol-5-yl | |
| $CH_2P(O)(OC_2H_5)_2$ | O | CH | 1,2,4-Oxadiazol-3-yl | |
| $CH_2P(O)(OC_2H_5)_2$ | O | CH | 1,2,4-Oxadiazol-5-yl | |
| $CH_2P(O)(OC_2H_5)_2$ | O | CH | 1,2,3,4-Thiatriazol-5-yl | |
| $CH_2P(O)(OC_2H_5)_2$ | O | CH | 2-Pyridyl | |
| $CH_2P(O)(OC_2H_5)_2$ | O | CH | 3-Pyridyl | |
| $CH_2P(O)(OC_2H_5)_2$ | O | CH | 4-Pyridyl | |
| $CH_2P(O)(OC_2H_5)_2$ | O | CH | 2-Naphthyl | |
| $CH_2P(O)(OC_2H_5)_2$ | O | CH | 1-Naphthyl | |
| $CH_2P(O)(OC_2H_5)_2$ | O | CH | 2-quinolinyl | |
| $CH_2P(O)(OC_2H_5)_2$ | O | CH | 4-quinolinyl | |
| $CH_2P(O)(OCH_3)_2$ | O | CH | 1-Pyrrolyl | |
| $CH_2P(O)(OCH_3)_2$ | O | CH | 1-Indolyl | |
| $CH_2P(O)(OCH_3)_2$ | O | CH | 2-Thienyl | |
| $CH_2P(O)(OCH_3)_2$ | O | CH | 3-Thienyl | |
| $CH_2P(O)(OCH_3)_2$ | O | CH | 2-bromo-5-thienyl | |
| $CH_2P(O)(OCH_3)_2$ | O | CH | 3-Methyl-2-thienyl | |
| $CH_2P(O)(OCH_3)_2$ | O | CH | 2-chloro-5-thienyl | |
| $CH_2P(O)(OCH_3)_2$ | O | CH | Benzthien-2-yl | |
| $CH_2P(O)(OCH_3)_2$ | O | CH | Benzthien-3-yl | |
| $CH_2P(O)(OCH_3)_2$ | O | CH | 2-Furanyl | |
| $CH_2P(O)(OCH_3)_2$ | O | CH | 3-Furanyl | |
| $CH_2P(O)(OCH_3)_2$ | O | CH | Benzofuran-2-yl | |
| $CH_2P(O)(OCH_3)_2$ | O | CH | 1-Pyrazolyl | |
| $CH_2P(O)(OCH_3)_2$ | O | CH | 1-Methyl-pyrazol-3-yl | |
| $CH_2P(O)(OCH_3)_2$ | O | CH | Benzpyrazol-1-yl | |
| $CH_2P(O)(OCH_3)_2$ | O | CH | 1-Imidazolyl | |
| $CH_2P(O)(OCH_3)_2$ | O | CH | 1-Methyl-imidazol-4-yl | |
| $CH_2P(O)(OCH_3)_2$ | O | CH | Benzimidazol-1-yl | |
| $CH_2P(O)(OCH_3)_2$ | O | CH | 1,2,3-Triazol-1-yl | |
| $CH_2P(O)(OCH_3)_2$ | O | N | 1-Methyl-1,2,3-triazol-4-yl | |
| $CH_2P(O)(OCH_3)_2$ | O | CH | Benz-1,2,3-triazol-1-yl | |
| $CH_2P(O)(OCH_3)_2$ | O | CH | 1,2,4-Triazol-1-yl | |
| $CH_2P(O)(OCH_3)_2$ | O | CH | 1-Methyl-1,2,4-triazol-3-yl | |
| $CH_2P(O)(OCH_3)_2$ | O | CH | 1-Tetrazolyl | |
| $CH_2P(O)(OCH_3)_2$ | O | CH | 2-Oxazolyl | |
| $CH_2P(O)(OCH_3)_2$ | O | CH | 4-Oxazolyl | |
| $CH_2P(O)(OCH_3)_2$ | O | CH | 5-Oxazolyl | |
| $CH_2P(O)(OCH_3)_2$ | O | CH | Benzoxazol-2-yl | |
| $CH_2P(O)(OCH_3)_2$ | O | CH | Isoxazol-3-yl | |
| $CH_2P(O)(OCH_3)_2$ | O | CH | Isoxazol-4-yl | |
| $CH_2P(O)(OCH_3)_2$ | O | CH | Isoxazol-5-yl | |
| $CH_2P(O)(OCH_3)_2$ | O | CH | Benzisoxazol-3-yl | |
| $CH_2P(O)(OCH_3)_2$ | O | CH | 2-Thiazolyl | |
| $CH_2P(O)(OCH_3)_2$ | O | CH | 4-Thiazolyl | |
| $CH_2P(O)(OCH_3)_2$ | O | CH | 5-Thiazolyl | |
| $CH_2P(O)(OCH_3)_2$ | O | CH | Benzthiazol-2-yl | |
| $CH_2P(O)(OCH_3)_2$ | O | CH | Isothiazol-3-yl | |
| $CH_2P(O)(OCH_3)_2$ | O | CH | Isothiazol-4-yl | |
| $CH_2P(O)(OCH_3)_2$ | O | CH | Isothiazol-5-yl | |
| $CH_2P(O)(OCH_3)_2$ | O | CH | Benzisothiazol-3-yl | |
| $CH_2P(O)(OCH_3)_2$ | O | CH | 1,2,3-Thiadiazol-4-yl | |
| $CH_2P(O)(OCH_3)_2$ | O | CH | 1,2,3-Thiadiazol-5-yl | |
| $CH_2P(O)(OCH_3)_2$ | O | CH | 1,3,4-Thiadiazol-2-yl | |
| $CH_2P(O)(OCH_3)_2$ | O | CH | 1,3,4-Thiadiazol-5-yl | |
| $CH_2P(O)(OCH_3)_2$ | O | CH | 1,2,3-Oxadiazol-4-yl | |

TABLE 2-continued

Compounds I in which $R^1$ is a radical $OR^5$ (R, $R^3$ = $OCH_3$, $R^4$ = H).

| $R^5$ | X | Z | A | Phys. data m.p. [°C.] |
|---|---|---|---|---|
| $CH_2P(O)(OCH_3)_2$ | O | CH | 1,2,3-Oxadiazol-5-yl | |
| $CH_2P(O)(OCH_3)_2$ | O | CH | 1,2,4-Oxadiazol-3-yl | |
| $CH_2P(O)(OCH_3)_2$ | O | CH | 1,2,4-Oxadiazol-5-yl | |
| $CH_2P(O)(OCH_3)_2$ | O | CH | 1,2,3,4-Thiatriazol-5-yl | |
| $CH_2P(O)(OCH_3)_2$ | O | CH | 2-Pyridyl | |
| $CH_2P(O)(OCH_3)_2$ | O | CH | 3-Pyridyl | |
| $CH_2P(O)(OCH_3)_2$ | O | CH | 4-Pyridyl | |
| $CH_2P(O)(OCH_3)_2$ | O | CH | 2-Naphthyl | |
| $CH_2P(O)(OCH_3)_2$ | O | CH | 1-Naphthyl | |
| $CH_2P(O)(OCH_3)_2$ | O | CH | 2-quinolinyl | |
| $CH_2P(O)(OCH_3)_2$ | O | CH | 4-quinolinyl | |

TABLE 3

Compounds I in which $R^1$ is a radical $NH-SO_2-R^{10}$ ($R^2$, $R^3$ = $OCH_3$, $R^4$ = H).

| $R^{10}$ | X | Z | A | Phys. data m.p. [°C.] |
|---|---|---|---|---|
| $CH_3$ | O | N | 1-Pyrrolyl | |
| $CH_3$ | O | CH | 1-Pyrrolyl | |
| $CH_3$ | S | CH | 1-Pyrrolyl | |
| $CH_3$ | O | N | 1-Methyl-pyrrol-2-yl | |
| $CH_3$ | O | CH | 1-Methyl-pyrrol-2-yl | |
| $CH_3$ | S | CH | 1-Methyl-pyrrol-2-yl | |
| $CH_3$ | O | N | 1-Methyl-pyrrol-3-yl | |
| $C_6H_4$-4-$CH_3$ | O | CH | 1-Methyl-pyrrol-3-yl | |
| $CH_3$ | S | CH | 1-Methyl-pyrrol-3-yl | |
| $C_6H_5$ | O | CH | 1-Indolyl | |
| $CH_3$ | O | CH | 1-Methyl-indol-2-yl | |
| $CH_3$ | O | CH | 1-Methyl-indol-3-yl | |
| $CH_3$ | O | CH | 3-Methyl-indol-1-yl | |
| $C_6H_4$-4-$CH_3$ | O | CH | 3,5-Dimethyl-pyrrol-1-yl | |
| $CH_3$ | O | CH | 3-Methylpyrrol-1-yl | |
| $CH_3$ | O | CH | 4-Methylpyrrol-1-yl | |
| $CH_3$ | O | CH | 4-chloropyrrol-1-yl | |
| $C_6H_5$ | O | CH | 4-Brompyrrol-1-yl | |
| $CH_3$ | O | CH | 4-Phenylpyrrol-1-yl | |
| $CH_3$ | O | CH | 3,4,5-Trimethyl-pyrrol-1-yl | |
| $CH_3$ | O | CH | 4-chloro-3,5-dimethyl-pyrrol-1-yl | |
| $C_6H_4$-4-$CH_3$ | O | CH | 4-Isopropylpyrrol-1-yl | |
| $CH_3$ | O | CH | 3-Phenylpyrrol-1-yl | |
| $CH_3$ | O | CH | 3-Methyl-5-phenyl-pyrrol-1-yl | |
| $C_6H_5$ | O | CH | 3,5-Bistrifluoromethyl-pyrrol-1-yl | |
| $CH_3$ | O | CH | 4-Nitropyrrol-1-yl | |
| $CH_3$ | O | CH | 1-Phenylpyrrol-3-yl | |
| $C_6H_4$-4-$CH_3$ | O | CH | 1,3,5-Trimethyl-pyrrol-4-yl | |
| $CH_3$ | O | CH | 1-Phenylpyrrol-2-yl | |
| $CH_3$ | O | CH | 1-Phenylpyrrol-3-yl | |
| $CH_3$ | O | CH | 1,4-Dimethylpyrrol-3-yl | |
| $C_6H_5$ | O | CH | 5-Methyl-1-phenyl-pyrrol-3-yl | |
| $CH_3$ | O | CH | 1,5-Dimethylpyrrol-3-yl | |
| $CH_3$ | O | CH | 1,3-Dimethylpyrrol-4-yl | |
| $CH_3$ | O | CH | 1,5-Dimethylpyrrol-3-yl | |
| $CH_3$ | O | CH | 3-Methyl-1-phenyl-pyrrol-4-yl | |
| $CH_3$ | O | CH | 5-Methyl-1-phenyl-pyrrol-2-yl | |
| $C_6H_5$ | O | CH | 3,5-Dimethyl-1-phenyl-pyrrol-4-yl | |
| $CH_3$ | O | CH | 3-Methyl-1-phenyl-pyrrol-5-yl | |
| $C_6H_4$-4-$CH_3$ | O | CH | 1,4-Dimethylpyrrol-5-yl | |
| $CH_3$ | O | CH | 1,3-Dimethylpyrrol-5-yl | |
| $CH_3$ | O | N | 2-Thienyl | |
| $CH_3$ | O | CH | 2-Thienyl | |
| $C_6H_5$ | S | CH | 2-Thienyl | |
| $CH_3$ | O | N | 3-Thienyl | |
| $CH_3$ | O | CH | 3-Thienyl | |
| $CH_3$ | S | CH | 3-Thienyl | |
| $CH_3$ | O | CH | 2,3-Dichloro-4-thienyl | |
| $C_6H_5$ | O | CH | 2,5-Dichloro-3-thienyl | |
| $CH_3$ | O | CH | 2-bromo-5-thienyl | |
| $CH_3$ | O | CH | 4-bromo-2-thienyl | |
| $C_6H_4$-4-$CH_3$ | O | CH | 3-Methyl-2-thienyl | |
| $CH_3$ | O | CH | 2-chloro-5-thienyl | |
| $CH_3$ | O | CH | 2-Methyl-5-thienyl | |
| $CH_3$ | O | CH | 2-Nitro-5-thienyl | |
| $CH_3$ | O | N | Benzthien-2-yl | |
| $CH_3$ | O | CH | Benzthien-2-yl | |
| $C_6H_5$ | S | CH | Benzthien-2-yl | |
| $CH_3$ | O | N | Benzthien-3-yl | |
| $C_6H_4$-4-$CH_3$ | O | CH | Benzthien-3-yl | |
| $CH_3$ | S | CH | Benzthien-3-yl | |
| $CH_3$ | O | N | 2-Furanyl | |
| $CH_3$ | O | CH | 2-Furanyl | |
| $CH_3$ | S | CH | 2-Furanyl | |
| $CH_3$ | O | N | 3-Furanyl | |
| $C_6H_5$ | O | CH | 3-Furanyl | |

TABLE 3-continued

Compounds I in which R¹ is a radical NH—SO₂—R¹⁰ (R², R³ = OCH₃, R⁴ = H).

| R¹⁰ | X | Z | A | Phys. data m.p. [°C.] |
|---|---|---|---|---|
| CH₃ | S | CH | 3-Furanyl | |
| CH₃ | O | CH | 2,3-Dichloro-4-furanyl | |
| CH₃ | O | CH | 2,5-Dichloro-3-furanyl | |
| CH₃ | O | CH | 2-bromo-5-furanyl | |
| CH₃ | O | CH | 4-bromo-2-furanyl | |
| CH₃ | O | CH | 3-Methyl-2-furanyl | |
| C₆H₄-4-CH₃ | O | CH | 2-chloro-5-furanyl | |
| C₆H₅ | O | CH | 2-Methyl-5-furanyl | |
| CH₃ | O | CH | 2-Nitro-5-furanyl | |
| CH₃ | O | N | Benzofuran-2-yl | |
| CH₃ | O | CH | Benzofuran-2-yl | |
| CH₃ | S | CH | Benzofuran-2-yl | |
| CH₃ | O | N | Benzofuran-3-yl | |
| C₆H₄-4-CH₃ | O | CH | Benzofuran-3-yl | |
| CH₃ | S | CH | Benzofuran-3-yl | |
| CH₃ | O | N | 1-Pyrazolyl | |
| CH₃ | O | CH | 1-Pyrazolyl | |
| CH₃ | S | CH | 1-Pyrazolyl | |
| C₆H₅ | O | N | 1-Methyl-pyrazol-3-yl | |
| CH₃ | O | CH | 1-Methyl-pyrazol-3-yl | |
| CH₃ | S | CH | 1-Methyl-pyrazol-3-yl | |
| CH₃ | O | N | 1-Methyl-pyrazol-4-yl | |
| CH₃ | O | CH | 1-Methyl-pyrazol-4-yl | |
| C₆H₄-4-CH₃ | S | CH | 1-Methyl-pyrazol-4-yl | |
| CH₃ | O | N | 1-Methyl-pyrazol-5-yl | |
| CH₃ | O | CH | 1-Methyl-pyrazol-5-yl | |
| C₆H₅ | S | CH | 1-Methyl-pyrazol-5-yl | |
| CH₃ | O | CH | Benzpyrazol-1-yl | |
| CH₃ | O | CH | 1-Methyl-benzpyrazol-3-yl | |
| CH₃ | O | CH | 3,5-Dimethyl-pyrazol-1-yl | |
| CH₃ | O | CH | 3(5)-Methyl-pyrazol-1-yl | |
| C₆H₄-4-CH₃ | O | CH | 4-Methylpyrazol-1-yl | |
| CH₃ | O | CH | 4-chloropyrazol-1-yl | |
| C₆H₅ | O | CH | 4-bromopyrazol-1-yl | |
| CH₃ | O | CH | 4-Phenylpyrazol-1-yl | |
| CH₃ | O | CH | 3,4,5-Trimethyl-pyrazol-1-yl | |
| CH₃ | O | CH | 4-chloro-3,5-dimethyl-pyrazol-1-yl | |
| CH₃ | O | CH | 4-Isopropylpyrazol-1-yl | |
| C₆H₄-4-CH₃ | O | CH | 3(5)-Phenylpyrazol-1-yl | |
| CH₃ | O | CH | 3(5)-Methyl-5(3)-phenyl-pyrazol-1-yl | |
| C₆H₅ | O | CH | 3,5-Bistrifluoromethyl-pyrazol-1-yl | |
| CH₃ | O | CH | 4-Nitropyrazol-1-yl | |
| CH₃ | O | CH | 1-Phenylpyrazol-4-yl | |
| CH₃ | O | CH | 1,3,5-Trimethyl-pyrazol-4-yl | |
| CH₃ | O | CH | 1-Phenylpyrazol-5-yl | |
| CH₃ | O | CH | 1-Phenylpyrazol-3-yl | |
| C₆H₄-4-CH₃ | O | CH | 1,4-Dimethylpyrazol-3-yl | |
| CH₃ | O | CH | 5-Methyl-1-phenyl-pyrazol-3-yl | |
| C₆H₅ | O | CH | 1,5-Dimethylpyrazol-3-yl | |
| CH₃ | O | CH | 1,3-Dimethylpyrazol-4-yl | |
| CH₃ | O | CH | 1,5-Dimethylpyrazol-4-yl | |
| CH₃ | O | CH | 3-Methyl-1-phenyl-pyrazol-4-yl | |
| CH₃ | O | CH | 5-Methyl-1-phenyl-pyrazol-4-yl | |
| C₆H₄-4-CH₃ | O | CH | 3,5-Dimethyl-1-phenyl-pyrazol-4-yl | |
| CH₃ | O | CH | 3-Methyl-1-phenyl-pyrazol-5-yl | |
| CH₃ | O | CH | 1,4-Dimethylpyrazol-5-yl | |
| CH₃ | O | CH | 1,3-Dimethylpyrazol-5-yl | |
| CH₃ | O | N | 1-Imidazolyl | |
| CH₃ | O | CH | 1-Imidazolyl | |
| CH₃ | S | CH | 1-Imidazolyl | |
| C₆H₄-4-CH₃ | O | N | 1-Methyl-imidazol-2-yl | |
| C₆H₅ | O | CH | 1-Methyl-imidazol-2-yl | |
| CH₃ | S | CH | 1-Methyl-imidazol-2-yl | |
| CH₃ | O | N | 1-Methyl-imidazol-4-yl | |
| CH₃ | O | CH | 1-Methyl-imidazol-4-yl | |
| CH₃ | S | CH | 1-Methyl-imidazol-4-yl | |
| CH₃ | O | N | 1-Methyl-imidazol-5-yl | |
| C₆H₅ | O | CH | 1-Methyl-imidazol-5-yl | |
| CH₃ | S | CH | 1-Methyl-imidazol-5-yl | |
| CH₃ | O | CH | Benzimidazol-1-yl | |
| C₆H₄-4-CH₃ | O | CH | 1-Methyl-benzimidazol-2-yl | |
| CH₃ | O | CH | 4,5-Dimethylimidazol-1-yl | |
| CH₃ | O | CH | 2-Phenylimidazol-1-yl | |
| CH₃ | O | CH | 4,5-Dichloroimidazol-1-yl | |
| CH₃ | O | CH | 2,4,5-Trichloro-imidazol-1-yl | |
| CH₃ | O | CH | 2-Methyl-4,5-dichloro-imidazol-1-yl | |
| C₆H₅ | O | CH | 2-Methyl-4,5-dibromo-imidazol-1-yl | |
| CH₃ | O | CH | 4(5)-chloro-5(4)-methyl-imidazol-1-yl | |
| C₆H₄-4-CH₃ | O | CH | 4(5)-Nitroimidazol-1-yl | |
| CH₃ | O | CH | 1,4-Dimethyl-imidazol-5-yl | |
| CH₃ | O | CH | 1-Methyl-5-nitro-imidazol-2-yl | |
| CH₃ | O | CH | 1-Phenylimidazol-5-yl | |
| CH₃ | O | N | 1,2,3,-Triazol-1-yl | |
| CH₃ | O | CH | 1,2,3-Triazol-1-yl | |
| CH₃ | S | CH | 1,2,3-Triazol-1-yl | |
| CH₃ | O | N | 1-Methyl-1,2,3-triazol-4-yl | |
| C₆H₅ | O | CH | 1-Methyl-1,2,3-triazol-4-yl | |
| CH₃ | S | CH | 1-Methyl-1,2,3-triazol-4-yl | |
| C₆H₄-4-CH₃ | O | N | 1-Methyl-1,2,3-triazol-5-yl | |
| CH₃ | O | CH | 1-Methyl-1,2,3-triazol-5-yl | |
| CH₃ | S | CH | 1-Methyl-1,2,3-triazol-5-yl | |
| CH₃ | O | CH | Benz-1,2,3-triazol-1-yl | |
| CH₃ | O | CH | 4,5-Dimethyl-1,2,3-triazol-1-yl | |
| CH₃ | O | CH | 4(5)-Phenyl-1,2,3-triazol-1-yl | |
| C₆H₅ | O | CH | 1-Phenyl-1,2,3-triazol-4-yl | |
| CH₃ | O | CH | 1-Phenyl-1,2,3-triazol-4-yl | |
| C₆H₄-4-CH₃ | O | CH | 5-Methyl-1-phenyl-1,2,3-triazol-4-yl | |
| CH₃ | O | N | 1,2,4-Triazol-1-yl | |
| CH₃ | O | CH | 1,2,4-Triazol-1-yl | |
| C₆H₅ | S | CH | 1,2,4-Triazol-1-yl | |
| CH₃ | O | N | 1-Methyl-1,2,4-triazol-3-yl | |
| CH₃ | O | CH | 1-Methyl-1,2,4-triazol-3-yl | |
| CH₃ | S | CH | 1-Methyl-1,2,4-triazol-3-yl | |
| CH₃ | O | N | 1-Methyl-1,2,4-triazol-5-yl | |
| CH₃ | O | CH | 1-Methyl-1,2,4-triazol-5-yl | |
| CH₃ | S | CH | 1-Methyl-1,2,4-triazol-5-yl | |
| C₆H₆-4-CH₃ | O | CH | 3(5)-Phenyl-1,2,4-triazol-1-yl | |
| CH₃ | O | CH | 3,5-Dimethyl-1,2,4-tiazol-1-yl | |
| C₆H₅ | O | CH | 5-Methyl-1-phenyl-1,2,4-triazol-3-yl | |
| CH₃ | O | N | 1-Tetrazolyl | |
| CH₃ | O | CH | 1-Tetrazolyl | |
| CH₃ | S | CH | 1-Tetrazolyl | |

TABLE 3-continued

Compounds I in which R¹ is a
radical NH—SO₂—R¹⁰ (R², R³ = OCH₃, R⁴ = H).

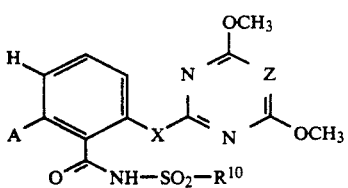
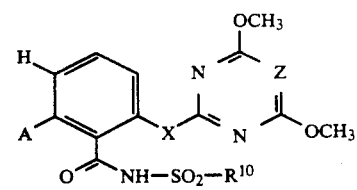

| R¹⁰ | X | Z | A | Phys. data m.p, [°C.] |
|---|---|---|---|---|
| CH₃ | O | N | 1-Methyl-tetrazol-5-yl | |
| CH₃ | O | CH | 1-Methyl-tetrazol-5-yl | |
| CH₃ | S | CH | 1-Methyl-tetrazol-5-yl | |
| CH₃ | O | N | 2-Oxazolyl | |
| C₆H₄-4-CH₃ | O | CH | 2-Oxazolyl | |
| CH₃ | S | CH | 2-Oxazolyl | |
| C₆H₅ | O | N | 4-Oxazolyl | |
| CH₃ | O | CH | 4-Oxazolyl | |
| CH₃ | S | CH | 4-Oxazolyl | |
| CH₃ | O | N | 5-Oxazolyl | |
| CH₃ | O | CH | 5-Oxazolyl | |
| CH₃ | S | CH | 5-Oxazolyl | |
| CH₃ | O | CH | 2-Methyloxazol-4-yl | |
| C₆H₄-4-CH₃ | O | CH | Benzoxazol-2-yl | |
| CH₃ | O | N | Isoxazol-3-yl | |
| CH₃ | O | CH | Isoxazol-3-yl | |
| C₆H₅ | S | CH | Isoxazol-3-yl | |
| CH₃ | O | N | Isoxazol-4-yl | |
| CH₃ | O | CH | Isoxazol-4-yl | |
| CH₃ | S | CH | Isoxazol-4-yl | |
| CH₃ | O | N | Isoxazol-5-yl | |
| CH₃ | O | CH | Isoxazol-5-yl | |
| CH₃ | S | CH | Isoxazol-5-yl | |
| C₆H₄-4-CH₃ | O | CH | Benzisoxazol-3-yl | |
| CH₃ | O | CH | 3-Methylisoxazol-5-yl | |
| CH₃ | O | CH | 3-Isopropylisoxazol-5-yl | |
| CH₃ | O | CH | 3-Phenylisoxazol-5-yl | |
| C₆H₅ | O | CH | 3-Methyl-4-chloro-isoxazol-5-yl | |
| CH₃ | O | CH | 3-Methylisoxazol-4-yl | |
| CH₃ | O | CH | 3,5-Dimethyl-isoxazol-4-yl | |
| CH₃ | O | N | 2-Thiazolyl | |
| CH₃ | O | CH | 2-Thiazolyl | |
| CH₃ | S | CH | 2-Thiazolyl | |
| C₆H₄-4-CH₃ | O | N | 4-Thiazolyl | |
| CH₃ | O | CH | 4-Thiazolyl | |
| C₆H₅ | S | CH | 4-Thiazolyl | |
| CH₃ | O | N | 5-Thiazolyl | |
| CH₃ | O | CH | 5-Thiazolyl | |
| CH₃ | S | CH | 5-Thiazolyl | |
| CH₃ | O | CH | Benzthiazol-2-yl | |
| CH₃ | O | CH | 2-Methylthiazol-4-yl | |
| CH₃ | O | CH | 2-Phenylthiazol-4-yl | |
| C₆H₅ | O | CH | 2-Benzylthiazol-4-yl | |
| CH₃ | O | CH | 5-chloro-2-phenyl-thiazol-4-yl | |
| CH₃ | O | CH | 4-Methylthiazol-2-yl | |
| CH₃ | O | CH | 5-Methylthiazol-2-yl | |
| C₆H₄-4-CH₃ | O | CH | 4-Phenylthiazol-2-yl | |
| CH₃ | O | CH | 4-Methylthiazol-5-yl | |
| CH₃ | O | CH | 2-Methylthiazol-5-yl | |
| CH₃ | O | CH | 2-Phenylthiazol-5-yl | |
| C₆H₅ | O | N | Isothiazol-3-yl | |
| CH₃ | O | CH | Isothiazol-3-yl | |
| CH₃ | S | CH | Isothiazol-3-yl | |
| CH₃ | O | N | Isothiazol-4-yl | |
| CH₃ | O | CH | Isothiazol-4-yl | |
| CH₃ | S | CH | Isothiazol-4-yl | |
| CH₃ | O | N | Isothiazol-5-yl | |
| C₆H₄-4-CH₃ | O | CH | Isothiazol-5-yl | |
| CH₃ | S | CH | Isothiazol-5-yl | |
| CH₃ | O | CH | Benzisothiazol-3-yl | |
| CH₃ | O | N | 1,2,3-Thiadiazol-4-yl | |
| CH₃ | O | CH | 1,2,3-Thiadiazol-4-yl | |
| C₆H₅ | S | CH | 1,2,3-Thiadiazol-4-yl | |
| CH₃ | O | N | 1,2,3-Thiadiazol-5-yl | |
| CH₃ | O | CH | 1,2,3-Thiadiazol-5-yl | |
| CH₃ | S | CH | 1,2,3-Thiadiazol-5-yl | |
| CH₃ | O | N | 1,3,4-Thiadiazol-2-yl | |
| CH₃ | O | CH | 1,3,4-Thiadiazol-2-yl | |
| C₆H₄-4-CH₃ | S | CH | 1,3,4-Thiadiazol-2-yl | |
| CH₃ | O | N | 1,3,4-Thiadiazol-5-yl | |
| CH₃ | O | CH | 1,3,4-Thiadiazol-5-yl | |
| CH₃ | S | CH | 1,3,4-Thiadiazol-5-yl | |
| C₆H₅ | O | CH | 5-Methyl-1,3,4-thiadiazol-2-yl | |
| CH₃ | O | CH | 5-Phenyl-1,3,4-thiadiazol-2-yl | |
| CH₃ | O | N | 1,2,3-Oxadiazol-4-yl | |
| CH₃ | O | CH | 1,2,3-Oxadiazol-4-yl | |
| CH₃ | S | CH | 1,2,3-Oxadiazol-4-yl | |
| CH₃ | O | N | 1,2,3-Oxadiazol-5-yl | |
| CH₃ | O | CH | 1,2,3-Oxadiazol-5-yl | |
| C₆H₄-4-CH₃ | S | CH | 1,2,3-Oxadiazol-5-yl | |
| C₆H₅ | O | N | 1,2,4-Oxadiazol-3-yl | |
| CH₃ | O | CH | 1,2,4-Oxadiazol-3-yl | |
| CH₃ | S | CH | 1,2,4-Oxadiazol-3-yl | |
| CH₃ | O | N | 1,2,4-Oxadiazol-5-yl | |
| CH₃ | O | CH | 1,2,4-Oxadiazol-5-yl | |
| CH₃ | S | CH | 1,2,4-Oxadiazol-5-yl | |
| CH₃ | O | N | 1,2,3,4-Thiatriazol-5-yl | |
| CH₃ | O | CH | 1,2,3,4-Thiatriazol-5-yl | |
| C₆H₅ | S | CH | 1,2,3,4-Thiatriazol-5-yl | |
| CH₃ | O | N | 2-Pyridyl | |
| CH₃ | O | CH | 2-Pyridyl | |
| CH₃ | S | CH | 2-Pyridyl | |
| CH₃ | O | N | 3-Pyridyl | |
| C₆H₄-4-CH₃ | O | CH | 3-Pyridyl | |
| CH₃ | S | CH | 3-Pyridyl | |
| CH₃ | O | N | 4-Pyridyl | |
| C₆H₅ | O | CH | 4-Pyridyl | |
| CH₃ | S | CH | 4-Pyridyl | |
| CH₃ | O | CH | 6-Methyl-2-pyridyl | |
| CH₃ | O | CH | 3-chloro-5-pyridyl | |
| CH₃ | O | CH | 5-chloro-2-pyridyl | |
| C₆H₄-4-CH₃ | O | N | 2-Naphthyl | |
| CH₃ | O | CH | 2-Naphthyl | |
| CH₃ | S | CH | 2-Naphthyl | |
| C₆H₅ | O | N | 1-Naphthyl | |
| CH₃ | O | CH | 1-Naphthyl | |
| CH₃ | S | CH | 1-Naphthyl | |
| CH₃ | O | CH | 2-Methyl-1-naphthyl | |
| CH₃ | O | CH | 2-Methoxy-1-naphthyl | |
| CH₃ | O | CH | 1-chloro-4-naphthyl | |
| CH₃ | O | N | 2-quinolinyl | |
| C₆H₅ | O | CH | 2-quinolinyl | |
| CH₃ | S | CH | 2-quinolinyl | |
| CH₃ | O | N | 4-quinolinyl | |
| C₆H₄-4-CH₃ | S | CH | 4-quinolinyl | |
| CH₃ | S | CH | 4-quinolinyl | |
| CH₃ | O | CH | 2-chloro-quinolin-2-yl | |
| C₆H₅ | O | CH | 2,6-Dichloro-quinolin-3-yl | |
| CH₃ | O | CH | 2-chloro-6-methyl-quinolin-3-yl | |

The herbicidal and growth-regulating compounds I according to the invention, or agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

The compounds I are generally suitable for the preparation of solutions, emulsions, pastes and oil dispersions to be sprayed direct. Examples of inert additives are mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthahexanol, cyclohexanone, chlorobenzene, isophorone, etc., and strongly polar solvents such as N,N-dimethylformamide, dimethyl sulfoxide, N-methylpyrrolidone, water, etc.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90, % by weight of active ingredient. The active ingredients are used in a purity of 90 to 100, and preferably from 95 to 100, % (according to the NMR spectrum).

The compounds I according to the invention may be formulated as follows:

I. 90 parts by weight of compound 1.001 is mixed with 10 parts by weight of N-methyl-alpha-pyrrolidone. A mixture is obtained which is suitable for application in the form of very fine drops.

II. 20 parts by weight of compound 1.001 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound 1.002 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound 1.002 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound 1.001 is well mixed with 3 parts by weight of the sodium salt of diisobutylnaphthalene-alpha-sulfonic acid, 17 parts by weight of the sodium salt of a lignin-sulfonic acid obtained from a sulfite water liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound 1.001 is intimately mixed with 97 parts by weight of particulate kaolin. A dust is obtained containing 3% by weight of the active ingredient.

VII. 30 parts by weight of compound 1.002 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound 1.002 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or the herbicidal and growth-regulating agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 3, preferably 0.005 to 0.5, kg of active ingredient per hectare.

The growth-regulating salicylic acid derivatives of the formula I may exercise a variety of influences on practically all plant development stages, and are therefore used as growth regulators. The diversity of action of growth regulators depends especially on a) the type and variety of plant;
b) the time applied, with reference to the development stage of the plants and the time of the year;
c) the place and method of application (seed treatment, soil treatment, application to foliage, or injection into tree trunks);
d) climatic factors, e.g., average temperature, amount of precipitation, day length and light intensity);
e) soil conditions (including fertilization);
f) the formulation of the active ingredient; and
g) the concentration at which the active ingredient is applied.

The active ingredients I according to the invention may be applied not only to the seed (as a dressing), but also to the soil, i.e., via the roots, and to the foliage by spraying.

As a result of the good tolerance by crop plants, the application rate when the active ingredients are used as growth regulators may vary within wide limits.

When the active ingredients are used for treating seed, amounts of from 0.001 to 50, and preferably from 0.01 to 10, g per kg of seed are generally required. For foliage and soil treatment, amounts of from 0.001 to 10, preferably from 0.01 to 3, and especially from 0.01 to 0.5, kg/ha are generally considered to be sufficient.

The active ingredients or the herbicidal agents containing them may be applied pre- or postemergence. If certain crop plants tolerate the active ingredients less well, application techniques may be used in which the that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 3, preferably 0.15 to 1.0, kg of active ingredient per hectare.

In view of the many application methods possible, the compounds according to the invention, or agents containing them, may be used in a further number of crop plants for removing unwanted plant growth. The following crops are given by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Triticum durum | durum wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn. |

| Botanical name | Common name |
|---|---|
| | maize |

The compounds of the formula I are of particular interest for controlling a large number of fungi in various crops, especially wheat, rye, barley, oats, rice, indian corn, lawns, cotton, soybeans, coffee, sugar cane, fruit and ornamentals in horticulture and viticulture, and in vegetables such as cucumbers, beans and cucurbits, and in the seed of these plants.

The novel compounds are particularly useful for controlling the following plant diseases:

Erysiphe graminis in cereals,
Erysiphe cichoracearum and Sphaerotheca fuliginea in cucurbits,
Podosphaera leucotricha in applies,
Uncinula necator in vines,
Puccinia species in cereals,
Rhizoctonia solani in cotton,
Ustilago species in cereals and sugar cane,
Venturia inaequalis (scab) in apples,
Helminthosporium species in cereals,
Septoria nodorum in wheat,
Botrytis cinerea (gray mold) in strawberries and grapes,
Cercospora arachidicola in groundnuts,
Pseudocercosporella herpotrichoides in wheat and barley,
Pyricularia oryzae in rice,
Phytophthora infestans in potatoes and tomatoes,
Fusarium and Verticillium species in various plants,
Plasmopara viticola in grapes,
Alternaria species in fruit and vegetables.

The compounds are applied by treating the fungi or the plants, seeds or materials to be protected against fungus attack, or the soil with a fungicidally effective amount of the active ingredients. They may be applied before or after infection of the materials, plants or seeds by the fungi.

The fungicidal agents generally contain from 0.1 to 95, and preferably from 0.5 to 90, wt % of active ingredient.

Depending on the type of effect desired, application rates vary from 0.02 to 3 kg of active ingredient per hectare. The novel compounds may also be used for protecting materials (timber), e.g., against Paecilomyces variotii.

For treating seed, active ingredient amounts of from 0.001 to 50, and preferably from 0.01 to 10, g per kg of seed are generally sufficient.

The agents, or the ready-to-use formulations prepared therefrom, such as solutions, emulsions, suspensions, powders, dusts, pastes or granules, are applied in known manner, for example by spraying, atomizing, dusting, scattering, treating seed, or by watering.

To increase the spectrum of action and to achieve synergistic effects, the compounds I may be mixed with each other, or mixed and applied together with numerous representations of other herbicidal or growth-regulating active ingredient groups. Examples of suitable components are diazines, 4H-3,1-benzoxazine derivatives, henzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, (hetero)- aryloxyphenoxypropionic acids and salts, esters, amides thereof, etc.

It may also be useful to apply the compounds I, either alone or in combination with other herbicides, in admixture with other crop protection agents, e.g., agents for combating pests or phytophatogenic fungi or bacteria. The compounds may also be mixed with solutions of mineral salts used to remedy nutritional or trace element deficiencies. Non-phytotoxic oils and oil concentrates may also be added.

Synthesis Instructions

EXAMPLE 1

General Instructions for the Preparation of Aromatic Carboxylic Acid Hydroxylamine Esters or Similar Compounds of the Formula I 3.2 mmol of sodium hydride is added to a mixture of 3.2 mmol of the aromatic 2-(4,6-dimethoxypyrimidin-2-yl)-oxycarboxylic acid concerned in 20 ml of dimethoxyethane; gas immediately evolves. The mixture is stirred for 1 hour at room temperature and then cooled to 0° C., and 3.5 mmol of oxalyl chloride is added. The mixture is stirred for 1 hour at 0° C., and about 30% of the solvent is evaporated under reduced pressure to remove excess oxalyl chloride. A solution of 4.2 mmol of the hydroxylamine in question or a comparable hydroxy compound in 10 ml of dimethoxyethane is added, followed by 3.2 mmol of pyridine, at 0° C., and the mixture is heated over a period of about 1 hour to room temperature. It is poured into 120 ml of cold water and extracted with methylene chloride. The organic phase is dried over sodium sulfate and evaporated down under reduced pressure. The substance which remains can be further purified by chromatography on silica gel.

EXAMPLE 2

General instructions for the preparation of aromatic carboxylic acid hydroxylamine esters or similar compounds of the formula I 1.75 g (10.8 mmol) of N,N'-carbonylbisimidazole is added to a solution of 10 mmol of the corresponding 6-hetaryl-2-(4,6-dimethoxypyrimidin-2-yloxy)benzoic acid in 30 ml if tetrahydrofuran. After the mixture has been stirred for 30 minutes at room temperature, 9.9 mmol of the corresponding hydroxy compound is added and the whole is stirred for a further 14 hours. The reaction mixture is then hydrolyzed with 300 ml of 1N phosphoric acid and the resulting mixture is extracted several times with methyl tert-butyl ether. The organic phases are dried over sodium sulfate and evaporated down under reduced pressure. The residue can be further purified by column chromatography or recrystallization.

EXAMPLE 3

General instructions for the preparation of aromatic carboxylic acid hydroxylamine esters or similar compounds of the formula I 1.75 g (10.8 mmol) of N,N'-carbonylbisimidazole is added to a solution of 10 mmol of the corresponding 6-hetarylsalicylic acid in 30 ml of dioxane. After the mixture has been stirred for 30 minutes at room temperature, 9.9 mmol of the corresponding hydroxy compound is added and the whole is stirred for a further 14 hours. The batch is then hydrolyzed with 300 ml of 1N phosphoric acid, and the resulting mixture is extracted several times with methyl tert-butyl ether. The organic phases are combined, dried over sodium sulfate and evaporated down under reduced pressure. The residue is taken up in 40 ml of dimethylformamide, and 280 mg of sodium hydride (85% in paraffin, 10 mmol) is added. After the mixture has been stirred for 30 minutes at room temperature, 1.97 g (9 mmol) of 4,6-dimethoxy-2-methylsulfonylpyrimidine is added and the mixture is stirred for 14 hours. The reaction mixture is poured into 300 ml of 0.1N phosphoric acid and extracted with diethyl ether. The ether phase is dried over sodium sulfate and evaporated down, and the residue is purified by column chromatography or recrystallization.

EXAMPLE 4

General instructions for the preparation of aromatic carboxylic acid hydroxylamine esters or similar compounds of the formula I At 10° C., 0.46 g (0.015 mol) of sodium hydride (80% strength) is added to a solution of 15 mmol of azolyl 6-hetarylsalicylate in 25 ml of anhydrous dimethylformamide, and the mixture is stirred for 3 hours at 30° C., 3.27 g (0.015 mol) of 2-methylsulfonyl-4,6-dimethoxypyrimidine is added and the mixture is stirred for 12 hours at room temperature. It is then introduced into 500 ml of water to which 2.5 ml of orthophosphoric acid has previously been added. The oil which separates out is taken up in ethyl acetate and dried over sodium sulfate. The greasy residue remaining after evaporation is purified by column chromatography or recrystallization.

EXAMPLE 5

6-Pyrazolyl-2-(4,6-dimethoxypyrimidin-2-yloxy)-1-(N,N-dimethylaminooxycarbonyl)-benzene At 10° C., 0.30 g (0.01 mol) of sodium hydride (80% strength) is added to a solution of 2.47 g (10 mmol) of 3-pyrazolyl-2-(N,N-dimethylaminooxycarbonyl)-phenol in 25 ml of anhydrous dimethylformamide, and the reaction mixture is stirred for 3 hours at 30° C. 2.18 g (0.01 mol) of 2-methylsulfonyl-4,6-dimethoxypyrimidine is added and the mixture is stirred for 12 hours at room temperature. The reaction mixture is introduced into 500 ml of water to which 2.5 ml of orthophosphoric acid has previously been added. The oil which separates out is taken up in ethyl acetate and dried over sodium sulfate. The greasy residue remaining after evaporation is purified to give a colorless solid.

EXAMPLE 6

6-(2-Thienyl)-2-(4,6-dimethoxypyrimidin-2-yloxy)-1-(N,N-dimethylaminooxycarbonyl)-benzene 3.2 mmol of sodium hydride is added to a mixture of 1.14 g (3.2 mmol) of 6-(2-thienyl)-2-(4,6-dimethoxypyrimidin-2-yl)-benzoic acid in 20 ml of dimethoxyethane, whereupon a gas immediately evolves. The mixture is stirred for 1 hour at room temperature and cooled to 0° C., and 3.5 mmol of oxalyl chloride is added. The mixture is stirred for 1 hour at 0° C., after which about 30% of the solvent is evaporated under reduced pressure to remove excess oxalyl chloride. A solution of 4.2 mmol of N,N-dimethylhydroxylamine in 10 ml of dimethoxyethane (from 230 mg of N,N-dimethylhydroxylamine hydrochloride and 332 g of pyridine) is then added, followed by 3.2 mmol of pyridine at 0° C., and the mixture is heated over a period of 1 hour to room temperature. The mixture is poured into 120 ml of cold water and extracted with methylene chloride. The organic phase is dried over sodium sulfate and evaporated down under reduced pressure. The oil which remains is further purified by chromatography on silica gel.

EXAMPLE 7

6-Imidazolyl-2-(3,5-dimethoxy-s-triazin-1-yloxy)-1-[(1-pyrazolyl)-oxycarbonyl]-benzene 1.75 g (10.8 mmol) of N,N'-carbonylbisimidazole is added to a solution of 1.88 g (10 mmol) of 6-imidazolylsalicylic acid in 30 ml of tetrahydrofuran. After the mixture has been stirred for 30 minutes at room temperature, 9.9 mmol of N-hydroxypyrazole is added and the mixture is stirred for a further 14 hours. The reaction mixture is then hydrolyzed with 300 ml of 1N phosphoric acid and the resulting mixture is extracted several times with methyl tert-butyl ether. The organic phases are dried over sodium sulfate and evaporated down under reduced pressure. The residue is taken up in 40 ml of dimethylformamide, and 280 mg of sodium hydride (85% strength in paraffin, 10 mmol) is added. After the mixture has been stirred for 30 minutes at room temperature, 1.58 g (9 mmol) of 1-chloro-3,5-dimethoxy-s-triazine is added and the whole is stirred for 14 hours. The batch is introduced into 300 ml of 0.1N phosphoric acid, and extracted with diethyl ether. The ether phase is dried over sodium sulfate and evaporated down, and the residue is purified by column chromatography.

EXAMPLE 8

6-(2-Thienyl)-2-(4,6-dimethoxytriazin-2-yloxy)-1-(N,N-dimethylaminooxycarbonyl)-benzene 4.4 g (20 mmol) of 6-(2-thienyl)-salicyclic acid is dissolved in 30 ml of thionyl chloride, and refluxed for 90 minutes. After the reaction mixture has cooled it is evaporated down. Toluene is added twice (100 ml each time) to remove the thionyl chloride, followed by evaporation. The residue is dissolved in 50 ml of toluene, and a solution of N,N-dimethylhydroxylamine (from 6.85 g of N,N-dimethylhydroxylamine hydrochloride, 15 g of potassium carbonate and 30 ml of toluene) is added; the mixture is stirred for 14 hours at room temperature. The solution is introduced into a mixture of 150 ml of water and 4.5 g of orthophosphoric acid, the mixture is extracted with ethyl acetate, and the combined organic phases are washed with water and saturated sodium chloride solution, dried over sodium sulfate and evaporated down. After drying using an oil pump there remains 5 g of a colorless oil, which is dissolved in 50 ml of DMF and to which 0.64 g of sodium hydride (85% strength) is added. After the mixture has been stirred for 30 minutes, 3.67 g (21 mmol) of chlorodimethoxytriazine is added and the whole is heated for 2 hours at 50° C. The solution is poured into 400 ml of water/5 ml of orthophosphoric acid, extracted with ethyl acetate, dried over sodium sulfate, evaporated down and chromatographed on silica gel. There is obtained 2.2 g of the product as a colorless viscous oil. $^1$H-NMR in CDCl$_3$, 270 MHz, δ in ppm: 2.58 (s, 6H), 3.99 (s, 6H), 7.0–7.6 (m, 6H) (active ingredient no. 1.002).

The structure given in the Tables 4 and 5 below describe particularly preferred active ingredients of the formula I, and may be prepared—with appropriate modifications of the starting materials—in accordance with the foregoing synthesis examples.

TABLE 4

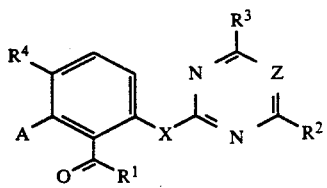

| No. | $R^1$ | A | $R^2$ | $R^3$ | $R^4$ | Z | X | Phys. data m.p. [°C.] $^1$H-NMR in CDCl$_3$, δ [ppm] |
|---|---|---|---|---|---|---|---|---|
| 1.001 | ON(CH$_3$)$_2$ | Thien-2-yl | OCH$_3$ | OCH$_3$ | H | CH | O | 102–112 |
| 1.002 | ON(CH$_3$)$_2$ | Thien-2-yl | OCH$_3$ | OCH$_3$ | H | N | o | 2,58(s, 6H), 3,99(s, 6H), 7,0–7,6(m, 6H) |

TABLE 5

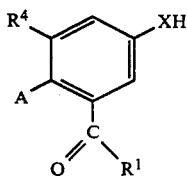

| No. | $R^1$ | A | $R^4$ | X | Phys. data m.p. [°C.] |
|---|---|---|---|---|---|
| 2.001 | ON(CH$_2$)$_2$ | Thienyl-2-yl | H | O | |

USE EXAMPLES

The herbicidal action of salicylic (thio)ether derivatives of the formula I is demonstrated in greenhouse experiments:

The vessels employed were plastic flowerpots having a volume of 300 cm$^3$ and filled with a sandy loam containing about 3.0% humus. The seeds of the test plants were sown separately, according to species.

For the preemergence treatment, the formulated active ingredients were applied to the surface of the soil immediately after the seeds had been sown. The compounds were emulsified or suspended in water as vehicle, and sprayed through finely distributing nozzles.

After the agents had been applied, the vessels were lightly sprinkler irrigated to induce germination and growth. Transparent plastic covers were then placed on the vessels until the plants had taken root. The cover ensured uniform germination of the plants, insofar as this was not impaired by the active ingredients.

For the postemergence treatment, plants were used which had been sown in the pots and grown there, or they were grown separately as seedlings and transplanted to the pots a few days before treatment. The plants were grown, depending on growth form, to a height of 3 to 15 cm before being treated with the compounds, suspended or emulsified in water. The application rate for postemergence treatment was 0.5 kg/ha.

The pots were set up in the greenhouse, heat-loving species at from 20° to 35° C., and species from moderate climates at from 10° to 25° C. The experiments were run for from 2 to 4 weeks. During this period the plants were tended and their reactions to the various treatments assessed. The assessment scale was 0 to 100, 100 denoting nonemergence or complete destruction of at least the visible plant parts, and 0 denoting no damage or normal growth.

The plants used in the greenhouse experiments were *Echinochloa crus-galli, Galium aparine* and *Centaurea cyanus*.

Active ingredients 1.001 and 1.002, applied postemergence at a rate of 0.05 kg/ha, give excellent control of unwanted plants.

We claim:
1. A salicyloyl(thio)ether derivative of the formula I

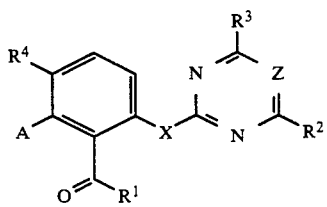

where
$R^1$ is a radical

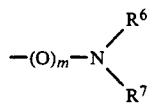

in which m is 0 or 1 and $R^6$ and $R^7$ are each hydrogen; C$_1$–C$_6$-alkyl, C$_3$–C$_6$-alkenyl, C$_3$–C$_6$-alkynyl, where these radicals may each carry from one to five halogen atoms and/or one or two of the following groups: C$_1$–C$_6$-alkoxy, C$_3$–C$_6$-alkenyloxy, C$_3$–C$_6$-alkynyloxy, C$_1$–C$_6$-alkylthio, C$_3$–C$_6$-alkenylthio, C$_3$–C$_6$-alkynylthio, C$_1$–C$_6$-haloalkoxy, cyano, C$_1$–C$_6$-alkylcarbonyl, C$_3$–C$_6$-alkenylcarbonyl, C$_3$–C$_6$-alkynylcarbonyl, C$_1$–C$_6$-alkoxycarbonyl, C$_3$–C$_6$-alkenyloxycarbonyl, C$_3$–C$_6$-alkynyloxycarbonyl, C$_1$–C$_6$-dialkylamino or C$_1$–C$_6$-cycloalkyl; unsubstituted or substituted C$_1$–C$_6$-cycloalkyl; unsubstituted or substituted phenyl;

$R^6$ together with $R^7$ may be an unsubstituted or substituted C$_4$–C$_7$-alkylene chain in which a CH$_2$ group may be replaced with oxygen, sulfur or —NH; a group

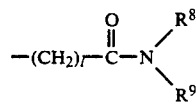

where $R^8$ and $R^9$ are each hydrogen, $C_1$-$C_4$-alkyl, $C_3$-$C_6$-alkenyl or $C_3$-$C_6$-alkynyl and l is 1, 2, 3 or 4; or a group $$-(CH_2)_l-S(=O)_k-R^{10}$$

where $R^{10}$ is $C_1$-$C_6$-alkyl, $C_3$-$C_6$-alkenyl or $C_3$-$C_6$-alkynyl, l is 1, 2, 3 or 4 and k is 0, 1 or 2; a radical $OR^5$, where $R^5$ is an unsubstituted or substituted 5-membered aromatic heterocyclic structure bonded via a nitrogen atom and having from one to four nitrogen atoms in the ring or a radical $$-(CH_2)_l-\overset{O}{\underset{OR^{11}}{\overset{\|}{P}}}-OR^{11}$$

where l is 1, 2, 3 or 4 and $R^{11}$ is alkyl, alkenyl or alkynyl as stated for $R^6$ and $R^7$, or a radical $$-NH-SO_2-R^{12}$$

where $R^{12}$ is $C_1$-$C_6$-alkyl, $C_1$-$C_6$-haloalkyl or phenyl, which in turn may carry from one to four of the following substituents: halogen, nitro, cyano or $C_1$-$C_6$-alkyl; $R^2$ and $R^3$ are each $C_1$-$C_4$-alkyl, $C_1$-$C_4$-haloalkyl, $C_1$-$C_4$-alkoxy, $C_1$-$C_4$-haloalkoxy and/or $C_1$-$C_4$-alkylthio; X is oxygen or sulfur;

Z is the methine group;

$R^4$ is hydrogen, halogen, nitro, $C_1$-$C_4$-alkyl, cyano or $C_1$-$C_4$-haloalkyl; and A is a 5-membered heteroaromatic structure having from one to four nitrogen atoms or from one to three nitrogen atoms and additionally a sulfur or oxygen atom in the ring, which may carry from one to three halogen atoms and/or from one to three of the following radicals: nitro, cyano, $C_1$-$C_4$-alkyl, $C_1$-$C_4$-alkylthio, $C_1$-$C_4$-haloalkyl or phenyl which is unsubstituted or substituted by from one to three halogen atoms and/or from one to three methyl groups; a benzofused 5-membered heteroaromatic structure which may contain from one to three nitrogen atoms or a nitrogen atom and additionally one oxygen or sulfur atom and may carry one of the following radicals: $C_1$-$C_4$-alkyl, halogen or cyano; a thienyl or furyl radical which may carry from one to three halogen atoms and/or from one to three of the following radicals: $C_1$-$C_4$-alkyl, $C_1$- or $C_2$-haloalkyl, a benzothienyl or benzofuryl radical which may carry one halogen atom and/or one of the following radicals: $C_1$-$C_4$-alkyl, $C_1$- or $C_2$-haloalkyl or nitro; pyridyl which may carry from one to three halogen atoms and/or from one to three of the following radicals: $C_1$-$C_4$-alkyl, $C_1$- or $C_2$-haloalkyl, unsubstituted or substituted phenyl or nitro; a naphthyl or quinolyl radical, each of which may carry up to three halogen atoms and/or up to three of the following radicals: $C_1$-$C_4$-alkyl or $C_1$- or $C_2$-haloalkyl, the expression unsubstituted or substituted in the abovementioned cases meaning that the corresponding groups may carry one or more of the following substituents: halogen, nitro, cyano, $C_1$-$C_6$-alkyl, $C_1$-$C_6$-haloalkyl, $C_1$-$C_6$-alkoxy or $C_1$-$C_6$-alkylthio.

2. A salicylic acid derivative of the formula I as defined in claim 1, where $R^1$ is a group $$-(O)_m-N\begin{smallmatrix}R^6\\\\R^7\end{smallmatrix}$$

where m is 0 or 1 and $R^6$ and $R^7$ are each hydrogen or methyl or $R^6$ and $R^7$ together form a $C_4$- or $C_5$-alkylene chain;

$R^2$ and $R^3$ are each methoxy, methyl, difluoromethoxy or $R^4$ is hydrogen or methyl;

X is oxygen;

Y is nitrogen;

Z is the methine group and

A has the meanings stated in claim 1.

3. A salicylic acid derivative of the formula I as defined in claim 1, wherein $R^1$ is $O-N(CH_3)_2$, X is oxygen, Y is nitrogen, Z is the methine group and $R^2$ and $R^3$ are each methoxy and A has the abovementioned meanings.

4. A herbicidal composition containing a compound of the formula I as defined in claim 1 and conventional inert additives.

5. A method for controlling undesirable plant growth, wherein the undesirable plants or their habitat is or are treated with a herbicidal amount of a derivative I as defined in claim 1.

6. A method for regulating plant growth, wherein an amount, having a regulatory effect, of a salicylic acid derivative of the formula I as defined in claim 1 is allowed to act on the seeds, the plants or their habitat.

7. A fungicide or nitrification inhibitor, containing a salicylic acid derivative of the formula I as defined in claim 1.

8. A salicylic acid derivative of the formula I as defined in claim 1, wherein $R^1$ is $ON(CH_3)_2$, A is thien-2-yl, $R^2$ and $R^3$ are each $OCH_3$, $R^4$ is hydrogen, Z is CH and X is oxygen.

9. A method for controlling undesirable plant growth, wherein the undesirable plants or their habitat is or are treated with a herbicidally effective amount of a derivative I as defined in claim 8.

* * * * *

UNITED STATES PATENT AND TRADEMARK OFFICE
CERTIFICATE OF CORRECTION

PATENT NO. : 5,246,914

DATED : September 21, 1993

INVENTOR(S) : VOGELBACHER et al.

It is certified that error appears in the above-identified patent and that said Letters Patent is hereby corrected as shown below:

Claim 1, column 63, line 1, "$C_1-C_4$-alkyl" should read --$C_1-C_6$-alkyl--.

line 23, "-NH-$SO_2$-$R^{12}$" should read -- -HN-$SO_2$-$R^{12}$ --.

line 50, between "$C_2$-haloalkyl," and "a" insert --unsubstituted or substituted phenyl or nitro;--.

Claim 2, column 64, line 22, insert --chlorine;-- after "thoxy or".

Signed and Sealed this

Twenty-ninth Day of March, 1994

Attest:

BRUCE LEHMAN

Attesting Officer      Commissioner of Patents and Trademarks